US009770491B2

(12) United States Patent
Beltran et al.

(10) Patent No.: US 9,770,491 B2
(45) Date of Patent: Sep. 26, 2017

(54) AAV-MEDIATED GENE THERAPY FOR RPGR X-LINKED RETINAL DEGENERATION

(71) Applicants: The Trustees of the University of Pennsylvania, Philadelphia, PA (US); University of Florida Research Foundation, Inc., Gainesville, FL (US)

(72) Inventors: William A Beltran, Philadelphia, PA (US); Gustavo D Aguirre, Philadelphia, PA (US); Samuel G Jacobson, Penn Valley, PA (US); Artur V Cideciyan, Philadelphia, PA (US); Alfred S Lewin, Gainesville, FL (US); Sanford L Boye, Gainesville, FL (US); William W Hauswirth, Gainesville, FL (US); Wen-Tao Deng, Gainesville, FL (US)

(73) Assignees: The Trustees of the University of Pennsylvania, Philadelphia, PA (US); Univeristy of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 14/413,884

(22) PCT Filed: Jan. 23, 2013

(86) PCT No.: PCT/US2013/022628
§ 371 (c)(1),
(2) Date: Jan. 9, 2015

(87) PCT Pub. No.: WO2014/011210
PCT Pub. Date: Jan. 16, 2014

(65) Prior Publication Data
US 2015/0202269 A1    Jul. 23, 2015

Related U.S. Application Data

(60) Provisional application No. 61/670,355, filed on Jul. 11, 2012.

(51) Int. Cl.
| C07H 21/04 | (2006.01) |
| A61K 48/00 | (2006.01) |
| A61K 38/46 | (2006.01) |
| C07K 14/47 | (2006.01) |
| A61K 38/17 | (2006.01) |
| A61K 38/18 | (2006.01) |
| C12N 15/86 | (2006.01) |
| A01K 67/00 | (2006.01) |

(52) U.S. Cl.
CPC .......... *A61K 38/46* (2013.01); *A61K 38/1709* (2013.01); *A61K 38/185* (2013.01); *A61K 48/005* (2013.01); *C07K 14/4702* (2013.01); *C12N 15/86* (2013.01); *A61K 48/00* (2013.01); *C12N 2750/14143* (2013.01); *C12N 2830/008* (2013.01); *C12Y 306/05* (2013.01)

(58) Field of Classification Search
CPC .. A61K 38/46; A61K 48/005; A61K 38/1709; A61K 38/185; A61K 48/00; C07K 14/4702; C12N 2750/14143; C12N 2830/008; C12N 15/86
See application file for complete search history.

(56) References Cited

U.S. PATENT DOCUMENTS

| 5,478,745 | A | 12/1995 | Samulski et al. |
| 5,939,534 | A | 8/1999 | Inoue et al. |
| 7,282,199 | B2 | 10/2007 | Gao et al. |
| 7,561,972 | B1 | 7/2009 | Welch et al. |
| 7,561,973 | B1 | 7/2009 | Welch et al. |
| 7,629,322 | B2 | 12/2009 | Kleinschmidt et al. |
| 7,888,112 | B2 | 2/2011 | Hermanson et al. |
| 2009/0202505 | A1 | 8/2009 | Bartus et al. |
| 2010/0081707 | A1* | 4/2010 | Ali ..................... A61F 9/0017 514/44 R |
| 2010/0272688 | A1 | 10/2010 | Acland et al. |
| 2010/0330042 | A1 | 12/2010 | De La Rosa Cano et al. |
| 2013/0024960 | A1* | 1/2013 | Nathwani ............ C07K 14/755 800/16 |

FOREIGN PATENT DOCUMENTS

| WO | WO02089857 A2 | 11/2002 |
| WO | WO-2005/033321 | 4/2005 |
| WO | WO-2010/097201 A1 | 2/2010 |

OTHER PUBLICATIONS

Lewin et al. AAV—mediated gene therapy in animal models of autosomal dominant and X-linked retinitis pigmentosa. Mol. Syndromol. 2: p. 265, 2011; Abstract A005_2012 (Published on line: Apr. 27, 2012).*
Vervoort et al. Mutational hot spot within a new RPGR exon in X-linked retinitis pigmentosa. Nature Gen. 25:462-466, 2000.*
Natkunarajah et al., "AAV Mediated Gene Replacement Therapy in the RPGR Knockout Mouse—A Model of X-Linked Retinitis Pigmentosa", Investigative Ophthalmology & Visual Science, vol. 46(Suppl. S): 5224, May 1, 2005.

(Continued)

*Primary Examiner* — Quang Nguyen
(74) *Attorney, Agent, or Firm* — Howson & Howson LLP

(57) ABSTRACT

Described herein are methods of preventing, arresting progression of or ameliorating vision loss and other conditions associated with retinitis pigmentosa and x-linked retinitis pigmentosa in a subject. The methods include administering to a subject an effective concentration of a composition comprising a recombinant adeno-associated virus (AAV) carrying a nucleic acid sequence encoding a normal retinitis pigmentosa GTPase regulator (RPGR gene), or fragment thereof, under the control of regulatory sequences which express the product of the gene in the photoreceptor cells of the subject, and a pharmaceutically acceptable carrier.

12 Claims, 10 Drawing Sheets

(56) References Cited

OTHER PUBLICATIONS

Dong-Hyun Hong et al., "A Single, Abbreviated RPGR-ORF15 Variant Reconstitutes RPGR Function In Vivo", Investigative Ophthalmology & Visual Science, vol. 46(2):435, Feb. 1, 2005.
Pang et al., "Comparative analysis of in vivo and in vitro AAV vector transduction in the neonatal mouse retina: Effects of serotype and site of administration", Vision Research, vol. 48(3), Oct. 22, 2007.
Beltran et al., "rAAV-mediated gene delivery of truncated canine RPGR causes retinal dysplasia in dogs with RPGR-ORF15 mutation", University of Pennsylvania—University of Florida, p. 1, May 1-5, 2011.
Beltran, "Assessment of rAAV-mediated gene delivery of RPGR in canine models of X-linked retinitis pigmentosa", ISOPT meeting presentation, Vienna Austria, pp. 1-24, Dec. 1-4, 2011.
Beltran et al., "Gene Augmentation for X-Linked Retinitis Pigmentosa Caused by Mutations in RPGR", Cold Spring Harbor Perspect Med, vol. 2015(5:a017392):1-17, Oct. 9, 2014.
Deng et al., Stability and Safety of an AAV Vector for Treating RPGR-ORF15 X-Linked Retinitis Pigmentosa, Human Gene Therapy, 26(9):593-602, Jun. 15, 2015.
Beltran et al., Gene therapy rescues photoreceptor blindness in dogs and paves the way for treating human X-linked retinitis pigmentosa. PNAS. vol. 109(6):2132-2137. Feb. 7, 2012. (ePub Jan. 23, 2012).
Beltran et al. A frameshift mutation in RPGR exon ORF15 causes photoreceptor degeneration and inner retina remodeling in a model of X-linked retinitis pigmentosa. IOVS. vol. 47(4):1669-1681, Apr. 2006.
Schmid et al. Mutation and tissue-specific alterations of RPGR transcripts. IOVS papers in press, manuscript iovs.09-4031. pp. 1-32. Oct. 2009.
Acland et al., Long-term restoration of rod and cone vision by single dose rAAV-mediated gene transfer to the retina in a canine model of childhood blindness, Mol Ther, vol. 12(6):1072-1082, Oct. 2005.
Aleman et al., Inner retinal abnormalities in X-linked retinitis pigmentosa with RPGR mutations, Invest Ophthalmol Vis Sci, vol. 48(10):4759-4765, Oct. 2007.
Alexander et al., Restoration of cone vision in a mouse model of achromatopsia, Nat Med, vol. 13(6):685-687, May 2007.
Alfinito et al., Activation of mislocalized opsin kills rod cells: a novel mechanism for rod cell death in retinal disease, PNAS, vol. 99(8):5655-5660, Apr. 2002.
Al-Ubaidi et al., Bilateral retinal and brain tumors in transgenic mice expressing simian virus 40 large T antigen under control of the human interphotoreceptor retinoid-binding protein promoter, J. Cell Biol, vol. 119(6):1681-1687, Dec. 1992.
Beltran et al., A frameshift mutation in RPGR exon ORF15 causes photoreceptor degeneration and inner retina remodeling in a model of X-linked retinitis pigmentosa, Invest Ophthalmol Vis Sci, vol. 47(4):1669-1681, Apr. 2006.
Beltran et al., Age-dependent disease expression determines remodeling of the retinal mosaic in carriers of RPGR exon ORF15 mutations, Invest Ophthalmol Vis Sci, vol. 50(8):3985-3995, Feb. 2009.
Beltran et al., rAAV2/5 gene-targeting to rods:dose-dependent efficiency and complications associated with different promoters, Gene Ther, vol. 17(9):1162-1174, Apr. 2010.
Bird, X-linked retinitis pigmentosa, Br J Ophthalmol, vol. 59(4):177-199, Apr. 1975.
Beltran et al., Gene therapy rescues photoreceptor blindness in dogs and paves the way for treating human X-linked retinitis pigmentosa, PNAS, vol. 109(6):2132-7, Jan. 2012.
Boatright et al., A major cis activator of the IRBP gene contains CRX-binding and Ret-1/PCE-I elements, Mol Vis, vol. 3(15):1-10, Dec. 1997.
Breuer et al., A comprehensive mutation analysis of RP2 and RPGR in a North American cohort of families with X-linked retinitis pigmentosa, Am J Hum Genet, vol. 70(6):1545-1554, Apr. 30, 2002.
Cai, A 350 bp region of the proximal promoter of Rds drives cell-type specific gene expression, Exp Eye Res, vol. 91(2):186-94, Aug. 2010.
Carvalho et al., Long-term and age-dependent restoration of visual function in a mouse model of CNGB3-associated achromatopsia following gene therapy, Hum Mol Genet, vol. 20(16):3161-3175, May 2011.
Chang et al., Retinal degeneration mutants in the mouse, Vision Res, vol. 42(4):517-525, Feb. 2002.
Cideciyan, Leber congenital amaurosis due to RPE65 mutations and its treatment with gene therapy, Prog Retin Eye Res, vol. 29(5):398-427, Sep. 2010.
Demirci et al., X-linked cone-rod dystrophy (locus COD1): identification of mutations in RPGR exon ORF15, Am J Hum Genet, vol. 70(4):1049-1053, Apr. 2002.
Fahim et al., Allelic heterogeneity and genetic modifier loci contribute to clinical variation in males with X-linked retinitis pigmentosa due to RPGR mutations, PLoS One, vol. 6(8):e23021, Aug. 2011.
Fisher et al., Transduction with recombinant adeno-associated virus for gene therapy is limited by leading-strand synthesis, J. Virol, vol. 70(1):520-532, Jan. 1996.
Geiger et al., Transgenic mice expression IFN-gamma in the retina develop inflammation of the eye and photoreceptor loss, Invest Ophthalmol Vis Sci, vol. 35(6):2667-2681, May 1994.
Genbank Accession No. AY327580, Jun. 23, 2003.
Ebenezer et al., Identification of novel RPGR ORF15 mutations in Xlinked progressive cone-rod dystrophy (XLCORD) families, Invest Ophthalmol Vis Sci, vol. 46(6):1891-1898, Jun. 2005.
Ghosh et al., Human retinopathy-assoicated ciliary protein Retinitis Pigmentosa GTPase Regulator mediates cilia-dependent vertebrate development, Hum Mol Genet, vol. 19(1):90-98, Jan. 2010.
Guyon et al., Analysis of six candidate genes as potential modifiers of disease expression in canine XLPRA1, a model for human X-linked retinitis pigmentosa 3, Mol Vis, vol. 13:1094-1105, Jul. 2007.
He et al., Retinitis Pigmentosa GTPase Regulator (RPGR) protein isoforms in mammalian retina: insights into X-linked Retinitis Pigmentosa and associated ciliopathies, Vision Res, vol. 48(3):366-376, Sep. 2008.
Hong et al., A retinitis pigmentosa GTPase regulator (RPGR)-deficient mouse model for X-linked retinitis pigmentosa (RP3), PNAS, vol. 97(7):3649-3654, Mar. 2000.
Hong et al., A single, abbreviated RPGR-ORF15 variant reconstitutes RPGR function in vivo, Invest Ophthalmol Vis Sci, vol. 46(2):435-441, Feb. 2005.
Hong et al., Complex expression pattern of RPGR reveals a role for purine-rich exonic splicing enhancers, Invest Opthamol Vis Sci, vol. 43(11):3373-82, Nov. 2002.
Hong et al., Dominant, gain-of-function mutant produced by truncation of RPGR, Invest Ophthalmol Vis Sci, vol. 45(1):36-41, Jan. 2004.
Jacobson et al., Disease boundaries in the retina of patients with Usher syndrome caused by MYO7A gene mutations, Invest Ophthalmol Vis Sci, vol. 50(4):1886-1894, Apr. 2009 (ePub Dec. 2008).
Jacobson et al., Disease expression in X-linked retinitis pigmentosa caused by a putative null mutation in the RPGR gene, Invest Ophthalmol Vis Sci, vol. 38(10):1983-1997, Sep. 1997.
Jacobson et al., Gene Therapy for Leber Congenital Amaurosis Caused by RPE65 Mutations: Safety and Efficacy in 15 Children and Adults Followed Up to 3 Years, Arch Ophthalmol E, vol. 130(1):9-24, Sep. 2011.
Jacobson et al., Human retinal disease from AIPL1 gene mutations: foveal cone loss with minimal masular photoreceptors and rod function remaining, Invest Ophthalmol Vis Sci, vol. 52(1):70-79, Jan. 2011.
Jacobson et al., Photoreceptor layer topography in children with leber congenital amaurosis caused by RPE65 mutations, Invest Ophthalmol Vis Sci, vol. 49(10):4573-4577, Jun. 2008.
Kachi, Equine infectious anemia viral vector-mediated codelivery of endostatin and angiostatin driven by retinal pigmented epithelium-specific VMD2 promoter inhibits choroidal neovascularization, Human Gene Ther, vol. 20(1):31-9, Jan. 2009.

(56) References Cited

OTHER PUBLICATIONS

Khanna et al., RPGR-ORF15, which is mutated in retinitis pigmentosa, associates with SMC1, SMC3, and microtubule transport proteins, J Biol Chem, vol. 280(39):33580-33587, Jul. 2005.
Kijas et al., Naturally occurring rhodopsin mutation in the dog causes retinal dysfunction and degeneration mimicking human dominant retinitis pigmentosa, PNAS, vol. 99(9):6328-6333, Apr. 2002.
Komaromy et al., Gene therapy rescues cone function in congenital achromatopsia, Hum Mol Genet, vol. 19(13):2581-2593, Apr. 2010.
Kozak et al., An analysis of 5'-noncoding sequences from 699 vertebrate messenger RNAs, Nucleic Acids Res., vol. 15(20):8125-8148, Oct. 1987.
Lambard, Expression of rod-derived cone viability factor: dual role of CRX in regulating promoter activity and cell-type specificity, PLosOne, vol. 5(10):e13025, Oct. 2010.
Li et al., Rod photoreceptor neurite sprouting in retinitis pigmentosa, J Neurosci, vol. 15(8):5429-5438, Aug. 1995.
Michalakis et al., Restoration of cone vision in the CNGA3-/- mouse model of congenital complete lack of cone photoreceptor function, Mol Ther, vol. 18(12):2057-2063, Jul. 2010.
Morrissey, PRE-1, a cis element sufficient to enhance cone- and rod-specific expression in differentiating zebrafish photoreceptors, BMC Dev Biol, vol. 11(3):1-12, Jan. 2011.
Mowat et al., Topographical characterization of cone photoreceptors and the area centralis of the canine retina, Mol Vis, vol. 14:2518-2527, Dec. 2008.
Murga-Zamalloa et al., Interaction of ciliary disease protein retinitis pigmentosa GTPase regulator with nephronophthisis-associated proteins in mammalian retinas, Mol Vis, vol. 16:1373-1381, Jul. 2010.
Murga-Zamalloa et al., Interaction of retinitis pigmentosa GTPase regulator (RPGR) with RAB8A GTPase: implications for cilia dysfunction and photoreceptor degeneration, Hum Mol Genet, vol. 19(18):3591-3598, Jul. 2010.
Mussolino, AAV-mediated photoreceptor transduction of the pig cone-enriched retina, Gene Ther, vol. 18(7):637-45, Jul. 2011 (ePub Mar. 2011).
Pelletier et al., Comprehensive survey of mutations in RP2 and RPGR in patients affected with distinct retinal dystrophies: genotype-phenotype correlations and impact on genetic counseling, Hum Mutat vol. 28(1):81-91, Jan. 2007.
Petrs-Silva et al., Novel properties of tyrosine-mutant AAV2 vectors in the mouse retina,Mol Ther, vol. 19(2):293-301, Nov. 2011.
Porrello et al., Detection of interphotoreceptor retinoid binding protein (IRBP) mRNA in human and cone-dominant squirrel retinas by in situ hybridization, J Histochem Cytochem, vol. 39(2):171-176, Feb. 1991.

Sandberg et al., Disease course of patients with X-linked retinitis pigmentosa due to RPGR gene mutations, Invest Ophthalmol Vis Sci, vol. 48(3):1298-1304, Mar. 2007.
Sharon et al., RP2 and RPGR Mutations and Clinical Correlations in Patients with X-Linked Retinitis Pigmentosa, Am J Hum Genet, vol. 73(5):1131-1146, Oct. 2003.
Shu et al., Functional characterization of the human RPGR proximal promoter, Invest Ophthalmol Vis Sci, vol. 53(7):3951-8, Jun. 2012.
Shu et al., RPGR ORF15 isoform co-localizes with RPGRIP1 at centrioles and basal bodies and interacts with nucleophosmin, Hum Mol Genet, vol. 14(9):1183-1197, Mar. 2005.
Sieving et al., Ciliary neurotrophic factor (CNTF) for human retinal degeneration: phase I trial of CNTF delivered by encapsulated cell intraocular implants, PNAS, vol. 103(10):3896-3901, Feb. 2006.
Simons et al., Gene therapy prevents photoreceptor death and preserves retinal function in a Bardet-Biedl syndrome mouse model, PNAS, vol. 108(15):6276-6281, Mar. 2011.
Vervoort, Mutations of RPGR in X-linked retinitis pigmentosa (RP3), Human Mutation, vol. 19(5):486-500, May 2002.
Walia et al., Discordant phenotypes in fraternal twins having an identical mutation in exon ORF15 of the RPGR gene, Arch Ophthalmol, vol. 126(3):379-384, Mar. 2008.
Wang, Sustained correction of bleeding disorder in hemophilia B mice by gene therapy, PNAS, vol. 96(7):3906-3910, Mar. 1999.
Weiss et al., Species-specific differences in expression of G-protein-coupled receptor kinase (GRK) 7 and GRK1 in mammalian cone photoreceptor cells: implications for cone cell phototransduction, J Neurosci, vol. 21(23):9175-9184, Dec. 2001.
Wright et al., Lifespan and mitochondrial control of neurodegeneration, Nat Genet, vol. 36(11):1153-1158, Nov. 2004.
Yang et al., Mutations in the RPGR gene cause X-linked cone dystrophy, Hum Mol Genet, vol. 11(5):605-611, Mar. 2002.
Zeiss et al., Retinal pathology of canine X-linked progressive retinal atrophy, the locus homologue of RP3, Investigative Ophthalmology & Visual Science, vol. 40(13):3292-3304, Dec. 1999.
Zhang et al., Cone opsin determines the time course of cone photoreceptor degeneration in Leber congenital amaurosis, PNAS, vol. 108(21):8879-8884, May 2011.
Zhang et al., Different RPGR exon ORF15 mutations in Canids provide insights into photoreceptor cell degeneration, Human Molecular Genetics, vol. 11(9):993-1003, May 2002.
Zolotukhin et al., Recombinant adeno-assoicated virus purification using novel methods improves infectious titer and yield, Gene Therapy, vol. 6(6):973-985, Jun. 1999.
Shu et al. GenBank: BK005711.1, also known as GenBank: DAA05713 retrieved from https://www.ncbi.nlm.nih.gov/nuccore/BK005711 on Mar. 23, 2017.(Feb. 3, 2006).

* cited by examiner

FIG. 3A

|  | 1 | | | | 50 |
|---|---|---|---|---|---|
| hRPGR_BK005711_(Wright) | ATGAGGGAGC | CGGAAGAGCT | GATGCCCGAT | TCGGGTGCTG | TGTTTACATT |
| hRPGR_Hauswirth/Boye | ATGAGGGAGC | CGGAAGAGCT | GATGCCCGAT | TCGGGTGCTG | TGTTTACATT |

|  | 51 | | | | 100 |
|---|---|---|---|---|---|
| hRPGR_BK005711_(Wright) | TGGGAAAAGT | AAATTTGCTG | AAAATAATCC | CGGTAAATTC | TGGTTTAAAA |
| hRPGR_Hauswirth/Boye | TGGGAAAAGT | AAATTTGCTG | AAAATAATCC | CGGTAAATTC | TGGTTTAAAA |

|  | 101 | | | | 150 |
|---|---|---|---|---|---|
| hRPGR_BK005711_(Wright) | ATGATGTCCC | TGTACATCTT | TCATGTGGAG | ATGAACATTC | TGCTGTTGTT |
| hRPGR_Hauswirth/Boye | ATGATGTCCC | TGTACATCTT | TCATGTGGAG | ATGAACATTC | TGCTGTTGTT |

|  | 151 | | | | 200 |
|---|---|---|---|---|---|
| hRPGR_BK005711_(Wright) | ACCGGAAATA | ATAAACTTTA | CATGTTTGGC | AGTAACAACT | GGGGTCAGTT |
| hRPGR_Hauswirth/Boye | ACCGGAAATA | ATAAACTTTA | CATGTTTGGC | AGTAACAACT | GGGGTCAGTT |

|  | 201 | | | | 250 |
|---|---|---|---|---|---|
| hRPGR_BK005711_(Wright) | AGGATTAGGA | TCAAAGTCAG | CCATCAGCAA | GCCAACATGT | GTCAAAGCTC |
| hRPGR_Hauswirth/Boye | AGGATTAGGA | TCAAAGTCAG | CCATCAGCAA | GCCAACATGT | GTCAAAGCTC |

|  | 251 | | | | 300 |
|---|---|---|---|---|---|
| hRPGR_BK005711_(Wright) | TAAAACCTGA | AAAAGTGAAA | TTAGCTGCCT | GTGGAAGGAA | CCACACCCTG |
| hRPGR_Hauswirth/Boye | TAAAACCTGA | AAAAGTGAAA | TTAGCTGCCT | GTGGAAGGAA | CCACACCCTG |

|  | 301 | | | | 350 |
|---|---|---|---|---|---|
| hRPGR_BK005711_(Wright) | GTGTCAACAG | AAGGAGGCAA | TGTATATGCA | ACTGGTGGAA | ATAATGAAGG |
| hRPGR_Hauswirth/Boye | GTGTCAACAG | AAGGAGGCAA | TGTATATGCA | ACTGGTGGAA | ATAATGAAGG |

|  | 351 | | | | 400 |
|---|---|---|---|---|---|
| hRPGR_BK005711_(Wright) | ACAGTTGGGG | CTTGGTGACA | CCGAAGAAAG | AAACACTTTT | CATGTAATTA |
| hRPGR_Hauswirth/Boye | ACAGTTGGGG | CTTGGTGACA | CCGAAGAAAG | AAACACTTTT | CATGTAATTA |

|  | 401 | | | | 450 |
|---|---|---|---|---|---|
| hRPGR_BK005711_(Wright) | GCTTTTTTAC | ATCCGAGCAT | AAGATTAAGC | AGCTGTCTGC | TGGATCTAAT |
| hRPGR_Hauswirth/Boye | GCTTTTTTAC | ATCCGAGCAT | AAGATTAAGC | AGCTGTCTGC | TGGATCTAAT |

|  | 451 | | | | 500 |
|---|---|---|---|---|---|
| hRPGR_BK005711_(Wright) | ACTTCAGCTG | CCCTAACTGA | GGATGGAAGA | CTTTTTATGT | GGGGTGACAA |
| hRPGR_Hauswirth/Boye | ACTTCAGCTG | CCCTAACTGA | GGATGGAAGA | CTTTTTATGT | GGGGTGACAA |

|  | 501 | | | | 550 |
|---|---|---|---|---|---|
| hRPGR_BK005711_(Wright) | TTCCGAAGGG | CAAATTGGTT | TAAAAAATGT | AAGTAATGTC | TGTGTCCCTC |
| hRPGR_Hauswirth/Boye | TTCCGAAGGG | CAAATTGGTT | TAAAAAATGT | AAGTAATGTC | TGTGTCCCTC |

|  | 551 | | | | 600 |
|---|---|---|---|---|---|
| hRPGR_BK005711_(Wright) | AGCAAGTGAC | CATTGGGAAA | CCTGTCTCCT | GGATCTCTTG | TGGATATTAC |
| hRPGR_Hauswirth/Boye | AGCAAGTGAC | CATTGGGAAA | CCTGTCTCCT | GGATCTCTTG | TGGATATTAC |

|  | 601 | | | | 650 |
|---|---|---|---|---|---|
| hRPGR_BK005711_(Wright) | CATTCAGCTT | TTGTAACAAC | AGATGGTGAG | CTATATGTGT | TTGGAGAACC |
| hRPGR_Hauswirth/Boye | CATTCAGCTT | TTGTAACAAC | AGATGGTGAG | CTATATGTGT | TTGGAGAACC |

|  | 651 | | | | 700 |
|---|---|---|---|---|---|
| hRPGR_BK005711_(Wright) | TGAGAATGGG | AAGTTAGGTC | TTCCCAATCA | GCTCCTGGGC | AATCACAGAA |
| hRPGR_Hauswirth/Boye | TGAGAATGGG | AAGTTAGGTC | TTCCCAATCA | GCTCCTGGGC | AATCACAGAA |

FIG. 3B

```
                            701                                                      750
    hRPGR_BK005711_(Wright)  CACCCCAGCT GGTGTCTGAA ATTCCGGAGA AGGTGATCCA AGTAGCCTGT
       hRPGR_Hauswirth/Boye  CACCCCAGCT GGTGTCTGAA ATTCCGGAGA AGGTGATCCA AGTAGCCTGT 751                                                      800
    hRPGR_BK005711_(Wright)  GGTGGAGAGC ATACTGTGGT TCTCACGGAG AATGCTGTGT ATACCTTTGG
       hRPGR_Hauswirth/Boye  GGTGGAGAGC ATACTGTGGT TCTCACGGAG AATGCTGTGT ATACCTTTGG 801                                                      850
    hRPGR_BK005711_(Wright)  GCTGGGACAA TTTGGTCAGC TGGGTCTTGG CACTTTTCTT TTTGAAACTT
       hRPGR_Hauswirth/Boye  GCTGGGACAA TTTGGTCAGC TGGGTCTTGG CACTTTTCTT TTTGAAACTT 851                                                      900
    hRPGR_BK005711_(Wright)  CAGAACCCAA AGTCATTGAG AATATTAGGG ATCAAACAAT AAGTTATATT
       hRPGR_Hauswirth/Boye  CAGAACCCAA AGTCATTGAG AATATTAGGG ATCAAACAAT AAGTTATATT 901                                                      950
    hRPGR_BK005711_(Wright)  TCTTGTGGAG AAAATCACAC AGCTTTGATA ACAGATATCG GCCTTATGTA
       hRPGR_Hauswirth/Boye  TCTTGTGGAG AAAATCACAC AGCTTTGATA ACAGATATCG GCCTTATGTA 951                                                     1000
    hRPGR_BK005711_(Wright)  TACTTTTGGA GATGGTCGCC ACGGAAAATT AGGACTTGGA CTGGAGAATT
       hRPGR_Hauswirth/Boye  TACTTTTGGA GATGGTCGCC ACGGAAAATT AGGACTTGGA CTGGAGAATT 1001                                                     1050
    hRPGR_BK005711_(Wright)  TTACCAATCA CTTCATTCCT ACTTTGTGCT CTAATTTTTT GAGGTTTATA
       hRPGR_Hauswirth/Boye  TTACCAATCA CTTCATTCCT ACTTTGTGCT CTAATTTTTT GAGGTTTATA 1051                                                     1100
    hRPGR_BK005711_(Wright)  GTTAAATTGG TTGCTTGTGG TGGATGTCAC ATGGTAGTTT TTGCTGCTCC
       hRPGR_Hauswirth/Boye  GTTAAATTGG TTGCTTGTGG TGGATGTCAC ATGGTAGTTT TTGCTGCTCC 1101                                                     1150
    hRPGR_BK005711_(Wright)  TCATCGTGGT GTGGCAAAAG AAATTGAATT CGATGAAATA AATGATACTT
       hRPGR_Hauswirth/Boye  TCATCGTGGT GTGGCAAAAG AAATTGAATT CGATGAAATA AATGACACTT 1151                                                     1200
    hRPGR_BK005711_(Wright)  GCTTATCTGT GGCGACTTTT CTGCCGTATA GCAGTTTAAC CTCAGGAAAT
       hRPGR_Hauswirth/Boye  GCTTATCTGT GGCGACTTTT CTGCCGTATA GCAGTTTAAC CTCAGGAAAT 1201                                                     1250
    hRPGR_BK005711_(Wright)  GTACTGCAGA GGACTCTATC AGCACGTATG CGGCGAAGAG AGAGGGAGAG
       hRPGR_Hauswirth/Boye  GTACTGCAGA GGACTCTATC AGCACGTATG CGGCGAAGAG AGAGGGAGAG 1251                                                     1300
    hRPGR_BK005711_(Wright)  GTCTCCAGAT TCTTTTTCAA TGAGGAGAAC ACTACCTCCA ATAGAAGGGA
       hRPGR_Hauswirth/Boye  GTCTCCAGAT TCTTTTTCAA TGAGGAGAAC ACTACCTCCA ATAGAAGGGA 1301                                                     1350
    hRPGR_BK005711_(Wright)  CTCTTGGCCT TTCTGCTTGT TTTCTCCCCA ATTCAGTCTT TCCACGATGT
       hRPGR_Hauswirth/Boye  CTCTTGGCCT TTCTGCTTGT TTTCTCCCCA ATTCAGTCTT TCCACGATGT 1351                                                     1400
    hRPGR_BK005711_(Wright)  TCTGAGAGAA ACCTCCAAGA GAGTGTCTTA TCTGAACAGG ACCTCATGCA
       hRPGR_Hauswirth/Boye  TCTGAGAGAA ACCTCCAAGA GAGTGTCTTA TCTGAACAGG ACCTCATGCA 1401                                                     1450
    hRPGR_BK005711_(Wright)  GCCAGAGGAA CCAGATTATT TGCTAGATGA AATGACCAAA GAAGCAGAGA
       hRPGR_Hauswirth/Boye  GCCAGAGGAA CCAGATTATT TGCTAGATGA AATGACCAAA GAAGCAGAGA 1451                                                     1500
    hRPGR_BK005711_(Wright)  TAGATAATTC TTCAACTGTA GAAAGCCTTG GAGAAACTAC TGATATCTTA
       hRPGR_Hauswirth/Boye  TAGATAATTC TTCAACTGTA GAAAGCCTTG GAGAAACTAC TGATATCTTA
```

FIG. 3C

```
                          1501                                               1550
hRPGR_BK005711_(Wright)   AACATGACAC ACATCATGAG CCTGAATTCC AATGAAAAGT CATTAAAATT
    hRPGR_Hauswirth/Boye  AACATGACAC ACATCATGAG CCTGAATTCC AATGAAAAGT CATTAAAATT 1551                                               1600
hRPGR_BK005711_(Wright)   ATCACCAGTT CAGAAACAAA AGAAACAACA AACAATTGGG GAACTGACGC
    hRPGR_Hauswirth/Boye  ATCACCAGTT CAGAAACAAA AGAAACAACA AACAATTGGG GAACTGACGC 1601                                               1650
hRPGR_BK005711_(Wright)   AGGATACAGC TCTTACTGAA AACGATGATA GTGATGAATA TGAAGAAATG
    hRPGR_Hauswirth/Boye  AGGATACAGC TCTTACTGAA AACGATGATA GTGATGAATA TGAAGAAATG 1651                                               1700
hRPGR_BK005711_(Wright)   TCAGAAATGA AAGAAGGGAA AGCATGTAAA CAACATGTGT CACAAGGGAT
    hRPGR_Hauswirth/Boye  TCAGAAATGA AAGAAGGGAA AGCATGTAAA CAACATGTGT CACAAGGGAT 1701                                               1750
hRPGR_BK005711_(Wright)   TTTCATGACG CAGCCAGCTA CGACTATCGA AGCATTTTCA GATGAGGAAG
    hRPGR_Hauswirth/Boye  TTTCATGACG CAGCCAGCTA CGACTATCGA AGCATTTTCA GATGAGGAAG 1751                                               1800
hRPGR_BK005711_(Wright)   TAGAGATCCC AGAGGAGAAG GAAGGAGCAG AGGATTCAAA AGGAAATGGA
    hRPGR_Hauswirth/Boye  TAGAGATCCC AGAGGAGAAG GAAGGAGCAG AGGATTCAAA AGGAAATGGA 1801                                               1850
hRPGR_BK005711_(Wright)   ATAGAGGAGC AAGAGGTAGA AGCAAATGAG GAAAATGTGA AGGTGCATGG
    hRPGR_Hauswirth/Boye  ATAGAGGAGC AAGAGGTAGA AGCAAATGAG GAAAATGTGA AGGTGCATGG 1851                                               1900
hRPGR_BK005711_(Wright)   AGGAAGAAAG GAGAAAACAG AGATCCTATC AGATGACCTT ACAGACAAAG
    hRPGR_Hauswirth/Boye  AGGAAGAAAG GAGAAAACAG AGATCCTATC AGATGACCTT ACAGACAAAG 1901                                               1950
hRPGR_BK005711_(Wright)   CAGAGGTGAG TGAAGGCAAG GCAAAATCAG TGGGAGAAGC AGAGGATGGG
    hRPGR_Hauswirth/Boye  CAGAGGTGAG TGAAGGCAAG GCAAAATCAG TGGGAGAAGC AGAGGATGGG 1951                                               2000
hRPGR_BK005711_(Wright)   CCTGAAGGTA GAGGGGATGG AACCTGTGAG GAAGGTAGTT CAGGAGCAGA
    hRPGR_Hauswirth/Boye  CCTGAAGGTA GAGGGGATGG AACCTGTGAG GAAGGTAGTT CAGGAGCAGA 2001                                               2050
hRPGR_BK005711_(Wright)   ACACTGGCAA GATGAGGAGA GGGAGAAGGG GGAGAAAGAC AAGGGTAGAG
    hRPGR_Hauswirth/Boye  ACACTGGCAA GATGAGGAGA GGGAGAAGGG GGAGAAAGAC AAGGGTAGAG 2051                                               2100
hRPGR_BK005711_(Wright)   GAGAAATGGA GAGGCCAGGA GAGGGAGAGA AGGAACTAGC AGAGAAGGAA
    hRPGR_Hauswirth/Boye  GAGAAATGGA GAGGCCAGGA GAGGGGGAGA AGGAACTAGC AGAGAAGGAA 2101                                               2150
hRPGR_BK005711_(Wright)   GAATGGAAGA AGAGGGATGG GGAAGAGCAG GAGCAAAAGG AGAGGGAGCA
    hRPGR_Hauswirth/Boye  GAATGGAAGA AGAGGGATGG GGAAGAGCAG GAGCAAAAGG AGAGGGAGCA 2151                                               2200
hRPGR_BK005711_(Wright)   GGGCCATCAG AAGGAAAGAA ACCAAGAGAT GGAGGAGGGA GGGGAGGAGG
    hRPGR_Hauswirth/Boye  GGGCCATCAG AAGGAAAGAA ACCAAGAGAT GGAGGAGGGA GGGGAGGAGG 2201                                               2250
hRPGR_BK005711_(Wright)   AGCATGGAGA AGGAGAAGAA GAGGAGGGAG ACAGAGAAGA GGAAGAAGAG
    hRPGR_Hauswirth/Boye  AGCATGGAGA AGGAGAAGAA GAGGAGGGAG ACAGAGAAGA GGAAGAAGAG
```

FIG 3D

```
                            2251                                              2300
hRPGR_BK005711_(Wright)     AAGGAGGGAG AAGGGAAAGA GGAAGGAGAA GGGGAAGAAG TGGAGGGAGA
    hRPGR_Hauswirth/Boye    AAGGAGGGAG AAGGGAAAGA GGAAGGAGAA GGGGAAGAAG TGGAGGGAGA 2301                                              2350
hRPGR_BK005711_(Wright)     ACGTGAAAAG GAGGAAGGAG AGAGGAAAAA GGAGGAAAGA GCGGGGAAGG
    hRPGR_Hauswirth/Boye    ACGTGAAAAG GAGGAAGGAG AGAGGAAAAA GGAGGAAAGA GCGGGGAAGG 2351                                              2400
hRPGR_BK005711_(Wright)     AGGAGAAAGG AGAGGAAGAA GGAGACCAAG GAGAGGGGGA AGAGGAGGAA
    hRPGR_Hauswirth/Boye    AGGAGAAAGG AGAGGAAGAA GGAGACCAAG GAGAGGGGGA AGAGGAGGAA 2401                                              2450
hRPGR_BK005711_(Wright)     ACAGAGGGGA GAGGGGAGGA AAAAGAGGAG GGAGGGGAAG TAGAGGGAGG
    hRPGR_Hauswirth/Boye    ACAGAGGGGA GAGGGGAGGA AAAAGAGGAG GGAGGGGAAG TAGAGGGAGG 2451                                              2500
hRPGR_BK005711_(Wright)     GGAAGTAGAG GAGGGGAAAG GAGAGAGGGA AGAGGAAGAG GAGGAGGGTG
    hRPGR_Hauswirth/Boye    GGAAGTAGAG GAGGGGAAAG GAGAGAGGGA AGAGGAAGAG GAGGAGGGTG 2501                                              2550
hRPGR_BK005711_(Wright)     AGGGGGAAGA GGAGGAAGGG GAGGGGGAAG AGGAGGAAGG GGAGGGGGAA
    hRPGR_Hauswirth/Boye    AGGGGGAAGA GGAGGAAGGG GAGGGGGAAG AGGAGGAA.. ....GG....

2551                                              2600
hRPGR_BK005711_(Wright)     GAGGAGGAAG GAGAAGGGAA AGGGGAGGAA GAAGGGGAAG AAGGAGAAGG
    hRPGR_Hauswirth/Boye    .......... .AGAAGGGAA AGGGGAGGAA GAAGGGGAAG AAGGAGAAGG 2601                                              2650
hRPGR_BK005711_(Wright)     GGAGGAAGAA GGGGAGGAAG GAGAAGGGGA GGGGGAAGAG GAGGAAGGAG
    hRPGR_Hauswirth/Boye    GGAGGAAGAA GGGGAGGAAG GAGAAGGGGA GGGGGAAGAG GAGGAAGGAG 2651                                              2700
hRPGR_BK005711_(Wright)     AAGGGGAGGG AGAAGAGGAA GGAGAAGGGG AGGGAGAAGA GGAGGAAGGA
    hRPGR_Hauswirth/Boye    AAGGGGAGGG AGAAGAGGAA GGAGAAGGGG AGGAAGAAG. ........GA 2701                                              2750
hRPGR_BK005711_(Wright)     GAAGGGGAGG GAGAAGAGGA AGGAGAAGGG GAGGGAGAAG AGGAGGAAGG
    hRPGR_Hauswirth/Boye    GAGGGAGAGG AAGAAGGGGA GGGAGAAGGG GAGGAAGAAG AGGA...AGG 2751                                              2800
hRPGR_BK005711_(Wright)     AGAAGGGAAA GGGGAGGAGG AAGGAGAGGA AGGAGAAGGG GAGGGGGAAG
    hRPGR_Hauswirth/Boye    GGAAGTGGAA GGGGAGGTGG AAGGGGAGGA AGGAGAGGGG GAAGGAGAGG 2801                                              2850
hRPGR_BK005711_(Wright)     AGGAGGAAGG AGAAGGGGAA GGGGAGGATG GAGAAGGGGA GGGGGAAGAG
    hRPGR_Hauswirth/Boye    AAGAGGAAGG AGAGGAGGAA GGAGAGGAAG AGGAAGGAGA GGAGGAAGGA 2851                                              2900
hRPGR_BK005711_(Wright)     GAGGAAGGAG AATGGGAGGG GGAGGAGGAA GGAGAAGGGG AGGGGGAAGA
    hRPGR_Hauswirth/Boye    GAGGAAGAGG AAGGAGAG.. .GAAGAGGAA GGAGA...GG AGGAAGGAGA 2901                                              2950
hRPGR_BK005711_(Wright)     GGAAGGAGAA GGGGAAGGGG AGGAAGGAGA AGGGGAGGGG GAAGAGGAGG
    hRPGR_Hauswirth/Boye    GGAAGGAGAA GGGGAGGGGG AAGAGGAGGA AGGAGAAGGG GAAGGGGAGG 2951                                              3000
hRPGR_BK005711_(Wright)     AAGGAGAAGG GGAGGGGGAA GAGGAGGAAG GGGAAGAAGA AGGGGAGGAA
    hRPGR_Hauswirth/Boye    ATGGAGAAGG GGAGGGGGAA GGAGAGGAAG AGGAAGGAGA GGAGGAAGGA 3001                                              3050
hRPGR_BK005711_(Wright)     GAAGGAGAGG GAGAGGAAGA AGGGGAGGGA GAAGGGGAGG AAGAAGAGGA
    hRPGR_Hauswirth/Boye    GAAGAAAGGG AAAAGGAGGG GGAAGGAGAG GAAGAGGAAG GAGAGGAGGA
```

FIG. 3E

|                          | 3051       |            |            |            | 3100       |
|--------------------------|------------|------------|------------|------------|------------|
| hRPGR_BK005711_(Wright)  | AGGGGAAGTG | GAAGGGGAGG | TGGAAGGGGA | GGAAGGAGAG | GGGGAAGGAG |
| hRPGR_Hauswirth/Boye     | AGGGGAAGTG | GAAGGGGAGG | TGGAAGGGGA | GGAAGGAGAG | GGGGAAGGAG |

|                          | 3101       |            |            |            | 3150       |
|--------------------------|------------|------------|------------|------------|------------|
| hRPGR_BK005711_(Wright)  | AGGAAGAGGA | AGGAGAGGAG | GAAGGAGAAG | AAAGGGAAAA | GGAGGGGGAA |
| hRPGR_Hauswirth/Boye     | AGGAAGAGGA | AGGAGAGGAG | GAAGGAGAAG | AAAGGGAAAA | GGAGGGGGAA |

|                          | 3151       |            |            |            | 3200       |
|--------------------------|------------|------------|------------|------------|------------|
| hRPGR_BK005711_(Wright)  | GGAGAAGAAA | ACAGGAGGAA | CAGAGAAGAG | GAGGAGGAAG | AAGAGGGGAA |
| hRPGR_Hauswirth/Boye     | GGAGAAGAAA | ACAGGAGGAA | CAGAGAAGAG | GAGGAGGAAG | AAGAGGGGAA |

|                          | 3201       |            |            |            | 3250       |
|--------------------------|------------|------------|------------|------------|------------|
| hRPGR_BK005711_(Wright)  | GTATCAGGAG | ACAGGCGAAG | AAGAGAATGA | AAGGCAGGAT | GGAGAGGAGT |
| hRPGR_Hauswirth/Boye     | GTATCAGGAG | ACAGGCGAAG | AAGAGAATGA | AAGGCAGGAT | GGAGAGGAGT |

|                          | 3251       |            |            |            | 3300       |
|--------------------------|------------|------------|------------|------------|------------|
| hRPGR_BK005711_(Wright)  | ACAAAAAAGT | GAGCAAAATA | AAAGGATCTG | TGAAATATGG | CAAACATAAA |
| hRPGR_Hauswirth/Boye     | ACAAAAAAGT | GAGCAAAATA | AAAGGATCTG | TGAAATATGG | CAAACATAAA |

|                          | 3301       |            |            |            | 3350       |
|--------------------------|------------|------------|------------|------------|------------|
| hRPGR_BK005711_(Wright)  | ACATATCAAA | AAAAGTCAGT | TACTAACACA | CAGGGAAATG | GGAAAGAGCA |
| hRPGR_Hauswirth/Boye     | ACATATCAAA | AAAAGTCAGT | TACTAACACA | CAGGGAAATG | GGAAAGAGCA |

|                          | 3351       |            |            |            | 3400       |
|--------------------------|------------|------------|------------|------------|------------|
| hRPGR_BK005711_(Wright)  | GAGGTCCAAA | ATGCCAGTCC | AGTCAAAACG | ACTTTTAAAA | AACGGGCCAT |
| hRPGR_Hauswirth/Boye     | GAGGTCCAAA | ATGCCAGTCC | AGTCAAAACG | ACTTTTAAAA | AACGGGCCAT |

|                          | 3401       |            |            |            | 3450       |
|--------------------------|------------|------------|------------|------------|------------|
| hRPGR_BK005711_(Wright)  | CAGGTTCCAA | AAAGTTCTGG | AATAATGTAT | TACCACATTA | CTTGGAATTG |
| hRPGR_Hauswirth/Boye     | CAGGTTCCAA | AAAGTTCTGG | AATAATGTAT | TACCACATTA | CTTGGAATTG |

|                          | 3451  |
|--------------------------|-------|
| hRPGR_BK005711_(Wright)  | AAGTAA |
| hRPGR_Hauswirth/Boye     | AAGTAA |

FIG. 4A

Alignment of amino acid sequence for human RPGR variant Hauswirth/Boye no top and variant BK005711(Wright) on bottom.

```
                              1                                                        50
    _hRPGR  Hauswirth/Boye    MREPEELMPD SGAVFTFGKS KFAENNPGKF WFKNDVPVHL SCGDEHSAVV
    hRPGR_(BK005711_Wright)   MREPEELMPD SGAVFTFGKS KFAENNPGKF WFKNDVPVHL SCGDEHSAVV 51                                                       100
    _hRPGR  Hauswirth/Boye    TGNNKLYMFG SNNWGQLGLG SKSAISKPTC VKALKPEKVK LAACGRNHTL
    hRPGR_(BK005711_Wright)   TGNNKLYMFG SNNWGQLGLG SKSAISKPTC VKALKPEKVK LAACGRNHTL 101                                                      150
    _hRPGR  Hauswirth/Boye    VSTEGGNVYA TGGNNEGQLG LGDTEERNTF HVISFFTSEH KIKQLSAGSN
    hRPGR_(BK005711_Wright)   VSTEGGNVYA TGGNNEGQLG LGDTEERNTF HVISFFTSEH KIKQLSAGSN 151                                                      200
    _hRPGR  Hauswirth/Boye    TSAALTEDGR LFMWGDNSEG QIGLKNVSNV CVPQQVTIGK PVSWISCGYY
    hRPGR_(BK005711_Wright)   TSAALTEDGR LFMWGDNSEG QIGLKNVSNV CVPQQVTIGK PVSWISCGYY 201                                                      250
    _hRPGR  Hauswirth/Boye    HSAFVTTDGE LYVFGEPENG KLGLPNQLLG NHRTPQLVSE IPEKVIQVAC
    hRPGR_(BK005711_Wright)   HSAFVTTDGE LYVFGEPENG KLGLPNQLLG NHRTPQLVSE IPEKVIQVAC 251                                                      300
    _hRPGR  Hauswirth/Boye    GGEHTVVLTE NAVYTFGLGQ FGQLGLGTFL FETSEPKVIE NIRDQTISYI
    hRPGR_(BK005711_Wright)   GGEHTVVLTE NAVYTFGLGQ FGQLGLGTFL FETSEPKVIE NIRDQTISYI 301                                                      350
    _hRPGR  Hauswirth/Boye    SCGENHTALI TDIGLMYTFG DGRHGKLGLG LENFTNHFIP TLCSNFLRFI
    hRPGR_(BK005711_Wright)   SCGENHTALI TDIGLMYTFG DGRHGKLGLG LENFTNHFIP TLCSNFLRFI 351                                                      400
    _hRPGR  Hauswirth/Boye    VKLVACGGCH MVVFAAPHRG VAKEIEFDEI NDTCLSVATF LPYSSLTSGN
    hRPGR_(BK005711_Wright)   VKLVACGGCH MVVFAAPHRG VAKEIEFDEI NDTCLSVATF LPYSSLTSGN 401                                                      450
    _hRPGR  Hauswirth/Boye    VLQRTLSARM RRRERERSPD SFSMRRTLPP IEGTLGLSAC FLPNSVFPRC
    hRPGR_(BK005711_Wright)   VLQRTLSARM RRRERERSPD SFSMRRTLPP IEGTLGLSAC FLPNSVFPRC 451                                                      500
    _hRPGR  Hauswirth/Boye    SERNLQESVL SEQDLMQPEE PDYLLDEMTK EAEIDNSSTV ESLGETTDIL
    hRPGR_(BK005711_Wright)   SERNLQESVL SEQDLMQPEE PDYLLDEMTK EAEIDNSSTV ESLGETTDIL 501                                                      550
    _hRPGR  Hauswirth/Boye    NMTHIMSLNS NEKSLKLSPV QKQKKQQTIG ELTQDTALTE NDDSDEYEEM
    hRPGR_(BK005711_Wright)   NMTHIMSLNS NEKSLKLSPV QKQKKQQTIG ELTQDTALTE NDDSDEYEEM 551                                                      600
    _hRPGR  Hauswirth/Boye    SEMKEGKACK QHVSQGIFMT QPATTIEAFS DEEVEIPEEK EGAEDSKGNG
    hRPGR_(BK005711_Wright)   SEMKEGKACK QHVSQGIFMT QPATTIEAFS DEEVEIPEEK EGAEDSKGNG 601                                                      650
    _hRPGR  Hauswirth/Boye    IEEQEVEANE ENVKVHGGRK EKTEILSDDL TDKAEVSEGK AKSVGEAEDG
    hRPGR_(BK005711_Wright)   IEEQEVEANE ENVKVHGGRK EKTEILSDDL TDKAEVSEGK AKSVGEAEDG 651                                                      700
    _hRPGR  Hauswirth/Boye    PEGRGDGTCE EGSSGAEHWQ DEEREKGEKD KGRGEMERPG EGEKELAEKE
    hRPGR_(BK005711_Wright)   PEGRGDGTCE EGSSGAEHWQ DEEREKGEKD KGRGEMERPG EGEKELAEKE 701                                                      750
    _hRPGR  Hauswirth/Boye    EWKKRDGEEQ EQKEREQGHQ KERNQEMEEG GEEEHGEGEE EEGDREEEEE
    hRPGR_(BK005711_Wright)   EWKKRDGEEQ EQKEREQGHQ KERNQEMEEG GEEEHGEGEE EEGDREEEEE
```

FIG. 4B

```
                        751                                                      800
 _hRPGR Hauswirth/Boye  KEGEGKEEGE GEEVEGEREK EEGERKKEER AGKEEKGEEE GDQGEGEEEE
hRPGR_(BK005711_Wright) KEGEGKEEGE GEEVEGEREK EEGERKKEER AGKEEKGEEE GDQGEGEEEE 801                                                      850
 _hRPGR Hauswirth/Boye  TEGRGEEKEE GGEVEGGEVE EGKGEREEEE EEGEGEEEEG EGEEEEGEG.
hRPGR_(BK005711_Wright) TEGRGEEKEE GGEVEGGEVE EGKGEREEEE EEGEGEEEEG EGEEEEGEGE 851                                                      900
 _hRPGR Hauswirth/Boye  ......KGEE EGEEGEGEEE GEEGEGEGEE EEGEGEGEEE GEGE...EEG
hRPGR_(BK005711_Wright) EEEGEGKGEE EGEEGEGEEE GEEGEGEGEE EEGEGEGEEE GEGEGEEEEG 901                                                      950
 _hRPGR Hauswirth/Boye  EGEEEGEGEG E.EEEEGEVE GEVEGEEGEG EGEEEEGEEE GEEEEGEEEG
hRPGR_(BK005711_Wright) EGEGEEEGEG EGEEEEGEGK GEEEGEEGEG EGEEEEGEGE GEDGEGEGEE 951                                                     1000
 _hRPGR Hauswirth/Boye  EEE..EGEEE EGEEEGEEGE GEGEEEEGEG EGEDGEGEGE GEEEEGEEEG
hRPGR_(BK005711_Wright) EEGEWEGEEE EGEGEGEE.E GEGEGEEGEG EGEEEEGEGE GEEEEGEEEG 1001                                                    1050
 _hRPGR Hauswirth/Boye  EER...EKEG EGEEEEGEEE GEVEGEVEGE EGEGEGEEEE GEEEEGEEREK
hRPGR_(BK005711_Wright) EEEGEGEEEG EGEGEE.EEE GEVEGEVEGE EGEGEGEEEE GEEEEGEEREK 1051                                                    1100
 _hRPGR Hauswirth/Boye  EGEGEENRRN REEEEEEEGK YQETGEEENE RQDGEEYKKV SKIKGSVKYG
hRPGR_(BK005711_Wright) EGEGEENRRN REEEEEEEGK YQETGEEENE RQDGEEYKKV SKIKGSVKYG 1101                                                    1150
 _hRPGR Hauswirth/Boye  KHKTYQKKSV TNTQGNGKEQ RSKMPVQSKR LLKNGPSGSK KFWNNVLPHY
hRPGR_(BK005711_Wright) KHKTYQKKSV TNTQGNGKEQ RSKMPVQSKR LLKNGPSGSK KFWNNILPHY 1151
 _hRPGR Hauswirth/Boye  LELK
hRPGR_(BK005711_Wright) LELK
```

FIG. 5

```
hRPGR Hauswirth/Boye  (845)                                                                                    (911)
hRPGR BK005711 Wright (845) EEGEG------KGEEEEGEEGEEEGEGEGEGEEGEGEEEGEGE---EEGEGEEEGEGE
Consensus             (845) EEGEGEEEGEGKGEEEGEEGEGEGEGEEGEGEEEGEGEEEGEGEEEGEGEEEGEGE
                            EEGEG      KGEEEGEEGEGEGEGEEGEGEGEGEEEGEGEEEGEGE   EEGEGE E EGEGE hRPGR Hauswirth/Boye  (912)                                                                                    (978)
hRPGR BK005711 Wright (902) -EEEEGEVEGEVEGEGEGEGEEEGEGEEEGEGEEEGEEE--EGEEEGEEEGEGEGEGEEEG
Consensus             (912) GEEEEGEGKGEEEGEEGEGEGEGEEEGEGEGEGEDGE GEGEEEGEWEGEEEEGEGEGEE-EGEGEGEEG
                            EEEEGE  GE EGEEGEGEGEGEEEEGE EGED EGE E EE  EGEEEEGE EGEE EGEGE EEG hRPGR Hauswirth/Boye  (979)                                                                                   (1045)
hRPGR BK005711 Wright (966) EGEGEDGEGEGEGEEEEGEGEEEGEER---EKEGEGEEEGEEEEGEVEGEVEGEEGEGEEEGEEEG
Consensus             (979) EGEGEEEEGEGEGEEEGEEEGEEGEEEGEEEGEGEE-EEEGEVEGEVEGEVEGEEGEGEEEEGEEEG
                            EGEGED EGEGEGE EGEGEEEGEEEGEE    E EGEGE EE EEEGEVEGEVEGEVEGEEGEGEEEEGEEEG hRPGR Hauswirth/Boye  (1046)           (1055)
hRPGR BK005711 Wright (1030) EEREKEGEGE
Consensus             (1044) EEREKEGEGE
                      (1046) EEREKEGEGE
```

AAV-MEDIATED GENE THERAPY FOR RPGR X-LINKED RETINAL DEGENERATION

CROSS-REFERENCE TO RELATED APPLICATIONS

This application is a US national phase of International Patent Application No. PCT/US2013/022628, filed Jan. 23, 2013, which claims the benefit of the priority of U.S. Provisional Patent Application No. 61/670,355, filed Jul. 11, 2012, now expired. These priority applications are incorporated by reference herein.

GOVERNMENT SUPPORT

This invention was made with government support under grant/contract numbers 5R01EY017549, 5R01EY006855, 1P30EY021721, 5R01EY007961, P30EY001583 and 5PN2EY018241 awarded by the National Institutes of Health. The government has certain rights in the invention.

BACKGROUND OF THE INVENTION

Photoreceptors function cooperatively with the retinal pigment epithelium (RPE) to optimize photon catch and generate signals that are transmitted to higher vision centers and perceived as a visual image. Disruption of the visual process in the retinal photoreceptors can result in blindness. Genetic defects in the retina cause substantial numbers of sight-impairing disorders by a multitude of mechanisms.

Among photoreceptor dystrophics, the X-linked forms of retinitis pigmentosa (XLRP) are one of the most common causes of severe vision loss. More than 25 years ago, the genetic loci were identified and discovery of the underlying gene defects followed. Human XLRP, caused by mutations in the Retinitis Pigmentosa GTPase Regulator (RPGR) gene, is a severe early onset retinal degenerative disease that accounts for the majority of XLRP. Mutations in the retinitis pigmentosa GTPase regulator (RPGR) gene account for >70% of the cases of XLRP, and exon ORF15, a mutational hot spot in RPGR, is mutated in 22-60% of patients. The disease is relentlessly progressive, and by the end of their fourth decade most patients are legally blind.

Until recently, progress has been slow in unraveling the molecular mechanisms that lead from mutation to PR degeneration, and in developing effective treatments for most forms of RP, including RPGR-XLRP. Disease-relevant animal models have been crucial in developing and validating new therapies. For RPGR-XLRP there are both mouse and canine models. In the dog, two naturally-occurring distinct microdeletions in ORF15 result in different disease phenotypes. X-linked progressive retinal atrophy 1 (XLPRA1; del 1028-1032) has a C-terminus truncation of 230 residues; the disease is juvenile, but post-developmental in onset, and progresses over several years. In contrast, the two-nucleotide deletion associated with XLPRA2 (del 1084-1085) causes a frameshift, and inclusion of 34 basic amino acids that changes the isoelectric point of the putative protein, and truncates the terminal 161 residues. The disease is early onset and rapidly progressive. Both models correspond to the disease spectrum of human XLRP, and, although differing in relative severity, they would be equivalent to human disease occurring within the first decade of life.

No successful treatment for XLRP is currently available to human patients suffering from this disease. What is needed is a treatment for RPGR-XLRP that is effective, safe and has long-term stability.

SUMMARY OF THE INVENTION

In one aspect, the invention provides a method of preventing, arresting progression of or ameliorating vision loss associated with retinitis pigmentosa in a subject. The method includes administering to the subject an effective concentration of a composition comprising a recombinant adeno-associated virus (rAAV) carrying a nucleic acid sequence encoding a normal RPGR gene, or fragment thereof, under the control of regulatory sequences which express the product of the gene in the ocular cells of the subject, and a pharmaceutically acceptable carrier.

In another aspect, a method of preventing or arresting progression of photoreceptor function loss, or increasing photoreceptor function in a subject in need thereof is provided. The method includes administering to the subject an effective concentration of a composition comprising a rAAV carrying a nucleic acid sequence encoding a normal RPGR gene, or fragment thereof, under the control of regulatory sequences which express the product of the gene in the subject's ocular cells, and a pharmaceutically acceptable carrier. As a result, the subject's vision is improved, or vision loss is arrested and/or ameliorated.

In another aspect, the invention provides a method of improving photoreceptor structure in a subject in need thereof. The method includes administering to the subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In yet another aspect, a method of preventing, arresting progression of or ameliorating outer plexiform layer (OPL) abnormalities in a subject in need thereof is provided. The method includes administering to the subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In another aspect, the invention provides a method of preventing, arresting progression of or ameliorating bipolar cell dendrite retraction in a subject in need thereof The method includes administering to the subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In another aspect, a method of preventing, arresting progression of or ameliorating bipolar cell function loss in a subject in need thereof is provided. The method includes administering to said subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In yet another embodiment, the invention provides a method of preventing, arresting progression of or ameliorating axonal injury characterized by overexpression of neurofilaments in a subject in need thereof. The method includes administering to the subject an effective concentration of a composition comprising a rAAV carrying a nucleic acid sequence encoding a normal RPGR gene, or fragment thereof under the control of regulatory sequences which express the product of the gene in the ocular cells of the subject, and a pharmaceutically acceptable carrier. As a result, the subject's vision is improved, or vision loss is arrested and/or ameliorated.

In another aspect, a method of preventing XLRP in a subject at risk of developing the disease is provided. The method includes administering to the subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier.

In yet another aspect, the invention provides a method of preventing, arresting or ameliorating rod and/or R/G cone opsin mislocalization in a subject in need thereof. The method includes administering to the subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In another aspect, the invention provides a method of preventing, arresting progression of or ameliorating OPL synaptic changes, bipolar cell abnormalities or inner retinal abnormalities associated with X-linked retinitis pigmentosa (XLRP) in a subject in need thereof. The method includes administering to the subject an effective concentration of a composition comprising a rAAV carrying a nucleic acid sequence encoding a normal RPGR gene, or fragment thereof, under the control of regulatory sequences which express the product of the gene in the subject's ocular cells, and a pharmaceutically acceptable carrier. As a result, the subject's vision is improved, or vision loss is arrested and/or ameliorated.

In yet another aspect, the invention provides a method of increasing or preserving ONL thickness associated with XLRP in a subject in need thereof. The method includes administering to said subject an effective concentration of a composition comprising a rAAV carrying a nucleic acid sequence encoding a normal RPGR gene, or fragment thereof, under the control of regulatory sequences which express the product of the gene in the ocular cells of the subject, and a pharmaceutically acceptable carrier. As a result, the subject's vision is improved, or vision loss is arrested and/or ameliorated.

In another aspect, a method of treating or preventing XLRP in a subject in need thereof is provided. The method includes (a) identifying subject having, or at risk of developing, XLRP; (b) performing genotypic analysis and identifying a mutation in the RPGR gene; (c) performing non-invasive retinal imaging and functional studies and identifying areas of retained photoreceptors that could be targeted for therapy; and (d) administering to the subject an effective concentration of a composition comprising a recombinant virus carrying a nucleic acid sequence encoding a normal photoreceptor cell-specific gene under the control of a promoter sequence which expresses the product of the gene in the ocular cells of the subject, and a pharmaceutically acceptable carrier, thereby preventing, arresting progression of or ameliorating XLRP.

In another aspect, the invention provides a composition comprising a recombinant adeno-associated virus (rAAV) carrying a nucleic acid sequence encoding a normal RPGR gene, or fragment thereof, under the control of regulatory sequences which express the product of the gene in the ocular cells of the subject, and a pharmaceutically acceptable carrier.

In another aspect, the invention provides a composition including a recombinant AAV2/5 psendotyped adeno-associated virus, carrying a nucleic acid sequence encoding a normal RPGR gene, or fragment thereof, under the control of a human IRBP or human GRK1 promoter which directs expression of the product of the gene in the ocular cells of the subject, formulated with a carrier and additional components suitable for injection. In another embodiment, any of the methods described above utilizes this composition.

BRIEF DESCRIPTION OF THE FIGURES

FIGS. 3A-3E are an alignment of the nucleic acid sequence encoding human RPGR variant SEQ ID NO: 1 (bottom) and the nucleic acid sequence encoding variant BK005711 (Wright) SEQ ID NO: 4 (top).

FIGS. 4A and 4B are an alignment of the amino acid sequence of human RPGR variant SEQ ID NO: 5 (top) and the amino acid sequence of variant BK005711 (Wright) SEQ ID NO: 6 (bottom).

FIG. 5 shows an alignment of amino acid residues aa 845-1039 of hRPGR variant of SEQ ID NO: 5, with amino acids residues 845 -1052 of the variant BK005711 of SEQ ID NO: 5, and further with the common amino acids forming a consensus sequence SEQ ID NO: 7. The consensus sequence in the alignment appears with gaps at the positions of non-consensus amino acids.

DETAILED DESCRIPTION OF THE INVENTION

Figure 1:
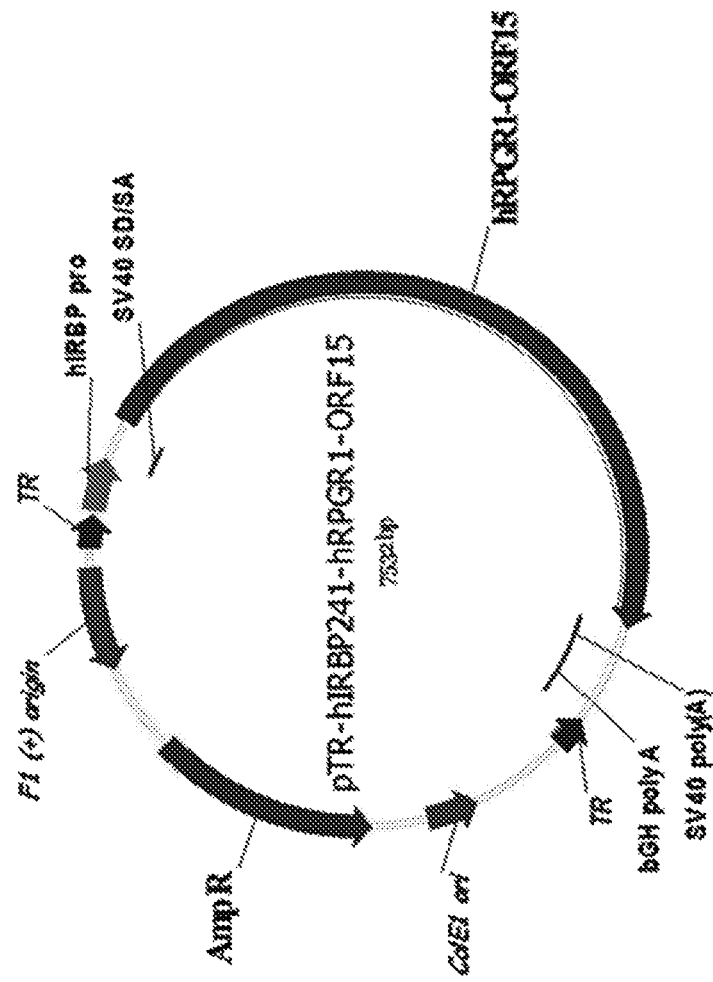
FIG. 1 is a plasmid map of the AAV2/5 vector incorporating the hIRPB promoter (SEQ ID NO: 2) and hRPGR1-ORF15 gene. The IRBP promoter in this plasmid is a 241 bp fragment of the proximal promoter region of the human IRBP gene.

The present invention relates to various compositions and treatment methods utilizing the same comprising an effective concentration of a recombinant adeno-associated virus (rAAV) carrying a nucleic acid sequence encoding a normal RPGR gene, or fragment thereof, under the control of regulatory sequences which direct expression of the product of the gene in the subject's ocular cells, formulated with a carrier and additional components suitable for injection. The treatment methods are directed to ocular disorders and associated conditions related thereto.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention.

The terms "a" or "an" refers to one or more, for example, "a gene" is understood to represent one or more such genes. As such, the terms "a" (or "an"), "one or more," and "at least one" are used interchangeably herein. As used herein, the term "about" means a variability of 10% from the reference given, unless otherwise specified. With regard to the following description, it is intended that each of the compositions herein described, is useful, in another embodiment, in the methods of the invention. In addition, it is also intended that each of the compositions herein described as useful in the methods, is, in another embodiment, itself an embodiment of the invention. While various embodiments in the specification are presented using "comprising" language, under other circumstances, a related embodiment is also intended to be interpreted and described using "consisting of" or "consisting essentially of" language.

A. The Mammalian Subject

As used herein, the term "mammalian subject" or "subject" includes any mammal in need of these methods of treatment or prophylaxis, including particularly humans. Other mammals in need of such treatment or prophylaxis include dogs, cats, or other domesticated animals, horses, livestock, laboratory animals, including non-human primates, etc. The subject may be male or female. In one embodiment, the subject has, or is at risk of developing, RP and more particularly, XLRP. In another embodiment, the subject is a "carrier" for XLRP, has at least one RPGR mutation in at least one X chromosome. Because XLRP is an X-linked disease, females, which normally have two X chromosomes, may be homozygous or heterozygous for a specific mutation in the RPGR gene, or compound heterozygotes, which have a different mutation in the RPGR gene on each X chromosome. Normal males, having only one X chromosome, with a mutation in the RPGR gene are termed hemizygous. In one embodiment, the subject having, or at risk of developing XLRP is a hemizygous male. In another embodiment, the subject having, or at risk of developing XLRP, is a homozygous female or a heterozygous female. In other embodiments, subjects at risk of developing XLRP include those with a family history of XLRP, those with one or more confirmed mutations in the RPGR gene, offspring of female carriers of an RPGR mutation (heterozygous females), or offspring of females carrying an RPGR mutation on both X chromosomes.

In another embodiment, the subject has shown clinical signs of XLRP. Clinical signs of XLRP include, but are not limited, to, decreased peripheral vision, decreased central (reading) vision, decreased night vision, loss of color perception, reduction in visual acuity, decreased photoreceptor function, pigmentary changes. In another embodiment, the subject has been diagnosed with XLRP. In yet another embodiment, the subject has not yet shown clinical signs of XLRP.

In yet another embodiment, the subject has 10% or more photoreceptor damage/loss. In another embodiment, the subject has 20% or more photoreceptor damage/loss. In another embodiment, the subject has 30% or more photoreceptor damage/loss. In another embodiment, the subject has 40% or more photoreceptor damage/loss. In another embodiment, the subject has 50% or more photoreceptor damage/loss. In another embodiment, the subject has 60% or more photoreceptor damage/loss. In another embodiment, the subject has 70% or more photoreceptor damage/loss. In another embodiment, the subject has 80% or more photoreceptor damage/loss. In another embodiment, the subject has 90% or more photoreceptor damage/loss.

B. XLRP and RPGR

In one aspect, the methods herein relate to the treatment or prevention of retinitis pigmentosa (RP). In an embodiment, the retinitis pigmentosa is an X-linked retinitis pigmentosa (XLRP). XLRP is one of the most severe forms of RP, demonstrating an early age of onset (usually within the first decade) and rapid progression of disease. Because the disease is X-linked, homozygous females are rare, usually only manifesting in small, isolated populations. Thus, the disease primarily affects males, although carrier (heterozygous) females are also affected, demonstrating various levels of retinal degeneration. The disease demonstrates a broad spectrum of disease severity, between and within families.

The retinitis pigmentosa GTPase regulator (RPGR) is an 815 aa protein which is implicated in XLRP (Meindl et al, Nature Genetics, 13:35-42 (May 1996) and Vervoort et al, Nature Genetics, 25:462-6 (2000), which are hereby incorporated by reference herein). Greater than 290 mutations in RPGR (http://rpgr.hgu.mrc.ac.uk/supplementary/, and document entitled "Summary of RPGR mutation and polymorphism", which is incorporated herein by reference) account for over 70% of XERP patients. The protein contains a RCC-1 like domain, characteristic of the highly conserved guanine nucleotide exchange factors. The constitutive transcript of RPGR, containing 19 exons, is expressed in a wide variety of tissues (Hong and Li, Invest Ophthalmology Vis Sci, 43(11):3373-82, incorporated by reference herein). An RPGR variant terminates in intron 15 of the RPGR gene. The alternative terminal exon consists of the constitutive exon 15 and part of intron 15, and is termed ORF15. This protein isoform that is encoded by exons 1 through ORF15 is used prevalently in photoreceptors and a large number of disease causing mutations have been found in ORF15 (Vervoort and Wright, Hum Mutat. 2002 May, 19(5):486-500; Aguirre et al, Exp Eye Res, 2002, 75:431-43; and Neidhardt et al, Hum Mutat. 2007, 28(8):797-807, each of which is hereby incorporated by reference herein).

In one aspect the method employs a nucleic acid sequence encoding a normal RPGR gene, or fragment thereof. The term "RPGR" as used herein, refers to the full length gene itself or a functional fragment, as farther defined below. The nucleic acid sequence encoding a normal RPGR gene may be derived from any mammal which natively expresses the RPGR gene, or homolog thereof. In another embodiment, the RPGR gene sequence is derived from the same mammal that the composition is intended to treat. In another embodiment, the RPGR is derived from a human. In another embodiment, the RPGR sequence is the sequence of the full length human RPGRORF15 clone, which includes exons 1 though ORF15 (Vervoort R, et al. (2000), Nat Genet 25:462-466, which is incorporated by reference herein). In another embodiment, the RPGR sequence is that shown in SEQ ID NO: 1. In another embodiment, the RPGR sequence is a functional fragment of the RPGRORF15 clone. By the term "fragment" or "functional fragment", it is meant any fragment that retains the function of the full length clone, although not necessarily at the same level of expression or activity. For example, acDNA representing RPGR-ORF15 but shortened by 654 bp in the repetitive region has been shown to reconstitute RPGR function in mice. (Hong, D. H. et al, Invest Ophthalmol Vis Sci 46(2): 435-441 which is hereby incorporated, by reference). Similar functional fragments of human, or other RPGR sequences may be determined by one of skill in the art. In another embodiment, the RPGR is derived from a canine. In other embodiments, certain modifications are made to the RPGR sequence in order to enhance the expression in the target cell. Such modifications include codon optimization, (see, e.g., U.S. Pat. Nos. 7,561,972; 7,561,973; and 7,888,112, incorporated herein by reference) and conversion of the sequence surrounding the translational start site to a consensus Kozak sequence: geeReeATGR. See, Kozak et al, *Nucleic Acids Res.* 15 (20): 8125-8148, incorporated herein by reference.

As used herein, the term "ocular cells" refers to any cell in, or associated with the function of, the eye. The term may refer to any one of photoreceptor cells, including rod, cone and photosensitive ganglion cells or retinal pigment epithelium (RPE) cells. In one embodiment, the ocular cells are the photoreceptor cells.

C. AAV Vectors and Compositions

In certain embodiments of this invention, the RPGR nucleic acid sequence, or fragment thereof, is delivered to the ocular cells in need of treatment by means of a viral vector, of which many are known and available in the art. For delivery to the ocular cells, the therapeutic vector is desirably non-toxic, non-immunogenic, easy to produce, and efficient in protecting and delivering DNA into the target cells. In one particular embodiment, the viral vector is an adeno-associated virus vector. In another embodiment, the invention provides a therapeutic composition comprising an adeno-associated viral vector comprising an RPGR sequence under the control of a suitable promoter. In one embodiment, the RPGR sequence is encoded by SEQ ID NO: 1.

More than 30 naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of RPGR nucleic acid sequences, for minimizing immunogenicity, for tuning stability and particle lifetime, for efficient degradation, for accurate delivery to the nucleus, etc.

Thus, RPGR overexpression can be achieved in the ocular cells through delivery by recombinantly engineered AAVs or artificial AAV's that contain sequences encoding RPGR. The use of AAVs is a common mode of exoamous delivery of DNA as it is relatively non-toxic, provides efficient gene transfer, and can be easily optimized for specific purposes. Among the serotypes AAVs isolated from human or non-human primates (NHP) and well characterized, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B. Other AAV serotypes include, but are not limited to, AAV1, AAV3, AAV4, AAV5, AAV6, AAV7, AAV8 and AAV9. See, e.g., WO 2005/033321 for a discussion of various AAV serotypes, which is incorporated herein by reference.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV non-AAV viral sequences. As used herein, artificial AAV serotypes include, without limitation, AAV with anon-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from anon-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. For illustrative purposes, AAV2/5 is used in the examples described below. In a preferred embodiment, the AAV is AAV2/5. In another preferred embodiment, the AAV is AAV2/8. See, Mussolino et al, cited above.

In one embodiment, the vectors useful in compositions and methods described herein contain, at a minimum, sequences encoding a selected AAV serotype capsid, e.g., an AAV5 capsid, or a fragment thereof. In another embodiment, useful vectors contain, at a minimum, sequences encoding a selected AAV serotype rep protein, e.g., AAV5 rep protein, or a fragment thereof. Optionally, such vectors may contain both AAV cap and rep proteins. In vectors in which both AAV rep and cap are provided, the AAV rep and AAV cap sequences can both be of one serotype e.g., all AAV5 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a RPGR nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. However, the required component(s) may be under the control of a constitutive promoter. Examples of suitable inducible and constitutive promoters are provided herein, in the discussion below of regulatory elements suitable for use with the transgene, i.e., RPGR. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 *J. Virol.*, 70:520-532 and U.S. Pat. No. 5,478,745, among others. These publications are incorporated by reference herein.

Unless otherwise specified, the AAV ITRs, and other selected AAV components described herein, may be readily selected from among any AAV serotype, including, without limitation, AAV1, AAV2, AAV3, AAV5, AAV6, AAV7, AAV8, AAV9 or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

The minigene is composed of, at a minimum, RPGR nucleic acid sequence (the transgene), as described above, and its regulatory sequences, and 5' and 3' AAV inverted terminal repeats (ITRs). In one desirable embodiment, the ITRs of AAV serotype 2 are used. However, ITRs from other suitable serotypes may be selected. It is this minigene which is packaged into a capsid protein and delivered to a selected host cell.

The regulatory sequences include conventional control elements which are operably linked to the RPGR acne in a manner which permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the constructs of the present invention may also contain an in tron, desirably located between the promoter/enhancer sequence and the gene. One desirable intron sequence is derived from SV-40, and is a 100 bp mini-intron splice donor/splice acceptor referred to as SD-SA. Another suitable sequence includes the woodchuck hepatitis virus post-transcriptional element. (See, e.g., L. Wang and I. Verma, 1999 Proc. Natl. Acad. Sci., USA, 96:3906-3910). PolyA signals may be derived from many suitable species, including, without limitation SV-40, human and bovine.

Another regulatory component of the rAAV useful in the method of the invention is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

The selection of the promoter to be employed in the rAAV may be made from among a wide number of constitutive or inducible promoters that can express the selected transgene in the desired an ocular cell. In another embodiment, the promoter is cell-specific. The term "cell-specific" means that the particular promoter selected for the recombinant vector can direct expression of the selected transgene in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In another embodiment, the promoter is specific for expression of the transgene RPE cells. In another embodiment, the transgene is expressed in any of the above noted ocular cells.

The promoter may be derived from any species. In another embodiment, the promoter is the human G-protein-coupled receptor protein kinase 1 (GRK1) promoter (Genbank Accession number AY327580). In another embodiment, the promoter is a 292 nt fragment (positions 1793-2087) of the GRK1 promoter (SEQ NO: 2) (See also, Beltran et al, Gene Therapy 2010 17:1162-74, which is hereby incorporated by reference herein). In another preferred embodiment, the promoter is the human interphotoreceptor retinoid-binding protein proximal (IRBP) promoter. In one embodiment, the promoter is a 235 nt fragment of the hIRBP promoter (SEQ NO: 3). In another embodiment, promoter is the native promoter for the gene to be expressed. In one embodiment, the promoter is the RPGR proximal promoter (Shu et al, IOVS, May 2102, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pimentosa (RP1) promoter (Nicord et al, J. Gene Med, December 2007, 9(12): 1015-23); the NXNL2,/NXNL1 promoter (Lombard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kochi et al, Human Gene Therapy, 2009(20:31-9)). Each of these documents is incorporated by reference herein. In one embodiment, the promoter is of a small size, under 1000 bp, due to the size limitations of the AAV vector. In another embodiment, the promoter is under 400 bp.

Examples of constitutive promoters useful in the invention include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the chicken β-actin (CBA) promoter, the phosphoglycerol kinase (PGK) promoter, the EF 1promoter (Invitrogen), and the immediate early CMV enhancer coupled with the CBA promoter (Beltran et al, Gene Therapy 2010 cited above).

Inducible promoters allow regulation of gene expression and can be regulated by exogenously supplied compounds, environmental factors such as temperature, or the presence of a specific physiological state, acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Other types of inducible promoters which may be useful in this context are those which are regulated by a specific physiological state, e.g., temperature, acute phase, a particular differentiation state of the cell, or in replicating cells only. Any type of inducible promoter which is tightly regulated and is specific for the particular target ocular cell type may be used.

Other regulatory sequences useful in the invention include enhancer sequences. Enhancer sequences useful in the invention include the IRBP enhancer (Nicord 2007, cited above), immediate early cytomegalovirus enhancer, one derived from an immunoglobulin gene or SV40 enhancer, the cis-acting element identified in the mouse proximal promoter, etc.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these, and other, expression control sequences without departing from the scope of this invention.

D. Pharmaceutical Compositions And Administration

The recombinant AAV containing the desired transgene and cell-specific promoter for use in the target ocular cells as detailed above is preferably assessed for contamination by conventional methods and then formulated into a pharmaceutical composition intended for subretinal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. Publication No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In certain embodiments of the methods of this invention, the pharmaceutical composition described above is administered to the subject by subretinal injection. The use of subretinal injection as the route of delivery is a critical component of this method, as intravitreal administration currently does not enable the same therapeutic effects.

Furthermore, in certain embodiments of the invention it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. These, and other desirable tests, are described in the examples below. In view of the imaging and functional studies, in some embodiments of the invention one or more injections are performed in the same eye in order to target different areas of retained photoreceptors. The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged photoreceptors is impacted. In another embodiment, the volume and/or concentration of the rAAV composition is a greater amount, in order reach larger portions of the eye, including non-damaged photoreceptors.

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL. An effective concentration of a recombinant adeno-associated virus carrying a nucleic acid sequence encoding the desired transgene under the control of the cell-specific promoter sequence desirably ranges between about $10^8$ and $10^{13}$ vector genomes per milliliter (vg/mL). The rAAV infectious units are measured as described in S. K. McLaughlin et al, 1988 J. Virol., 62:1963. Preferably, the concentration is from about $1.5 \times 10^9$ vg/mL to about $1.5 \times 10^{12}$ vg/mL, and more preferably from about $1.5 \times 10^9$ vg/mL to about $1.5 \times 10^{11}$ vg/mL. In one embodiment, the effective concentration is about $1.5 \times 10^{10}$ vg/mL. In another embodiment, the effective concentration is about $1.5 \times 10^{11}$ vg/mL. In another embodiment, the effective concentration is about $2.8 \times 10^{11}$ vg/mL. In yet another embodiment, the effective concentration is about $1.5 \times 10^{12}$ vg/mL. In another embodiment, the effective concentration is about $1.5 \times 10^{13}$ vg/mL. It is desirable that the lowest effective concentration of virus be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the particular ocular disorder and the degree to which the disorder, if progressive, has developed.

E. Methods of treatment/prophylaxis

The invention provides various methods of preventing, treating, arresting progression of or ameliorating the above-described ocular diseases and retinal changes associated therewith. Generally, the methods include administering to a mammalian subject in need thereof, an effective amount of a composition comprising a recombinant adeno-associated virus (AAV) carrying a nucleic acid sequence encoding a normal RPGR gene, or fragment thereof, under the control of regulatory sequences which express the product of the gene in the subject's ocular cells, and a pharmaceutically acceptable carrier.

RP, and more particularly, XLRP is associated with many retinal changes. These include a loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; loss of ERG function; loss of visual acuity and contrast sensitivity; and loss of visually guided behavior. In one embodiment, the invention provides a method of preventing, arresting progression of or ameliorating any of the retinal changes associated with XLRP. As a result, the subject's vision is improved, or vision loss is arrested and/or ameliorated.

In a particular embodiment, the invention provides a method of preventing, arresting progression of or ameliorating vision loss associated with retinitis pigmentosa in the subject. Vision loss associated with retinitis pigmentosa refers to any decrease in peripheral vision, central (reading) vision, night vision, day vision, loss of color perception, loss of contrast sensitivity, or reduction in visual acuity.

In another embodiment, the invention provides a method to prevent, or arrest photoreceptor function loss, or increase photoreceptor function in the subject. Photoreceptor function may be assessed using the functional studies described above and in the examples below, e.g., ERG or perimetry, which are conventional in the art. As used herein "photoreceptor function loss" means a decrease in photoreceptor function as compared to a normal, non-diseased eye or the same eye at an earlier time point As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient.

In another aspect, the invention provides method of improving photoreceptor structure in the subject. As used herein "improving photoreceptor structure" refers (in the region of the retina that is treated) to one or more of an increase or decrease in outer nuclear layer (ONL) thickness, or arresting progression of ONL thickening or thinning, across the entire retina, in the central retina, or the periphery; increase or decrease in outer plexiform layer (OPL) thickness, or arresting progression of OPL thickening or thinning, across the entire retina, in the central retina, or the periphery; decrease in rod and cone inner segment (IS) shortening; decrease in shortening and loss of outer segments (OS); decrease in bipolar cell dendrite retraction, or an increase in bipolar cell dendrite length or amount; and reversal of opsin mislocalization.

In another aspect, the invention provides a method of preventing, arresting progression of or ameliorating abnormalities of the outer plexiform layer (OPL) in a subject in need thereof. As used herein, to ameliorate abnormalities of the OPL means (in the region of the retina that is treated) to increase or decrease the OPL thickness, or arrest of OPL thickness changes, across the entire retina, in the central retina, or the periphery. In another aspect, the invention provides a method of increasing, decreaseing or preserving ONL thickness associated with X-linked form of retinitis pigmentosa (XLRP) in a subject in need thereof. Progressive ONL thinning is common in all phenotypes of XLRP, and is sometimes proceeded by abnormal ONL thickening As used herein, "increasing, decreasing or preserving ONL thickness" means to increase ONL thickness if it is thinner than normal, decrease ONL thickness if it is thicker than normal, or arresting progression of ONL thinning, across the entire retina, in the central retina, or the periphery. In another aspect, the invention provides a method of preventing, arresting progression of or ameliorating bipolar cell dendrite retraction in a subject in need thereof. In the course of XLRP progression, bipolar cell dendrites retract and fail to connect with photoreceptor cells. The inventors made the surprising discovery that, after treatment with the rAAV-RPGR construct described above, bipolar cells in damaged areas form new dendrites which are able to connect to the photoreceptor cells and improve function. Thus, in another embodiment, the invention provides a method of preventing, arresting progression of or ameliorating or improving bipolar cell function loss in a subject in need thereof. Enhancement of biolar function also leads to improved scotopic (rod mediated.) ERG b-wave amplitudes. In another embodiment, the invention provides a method of improving post receptoral responses for rods and cones as recorded by ERG. In another aspect, the invention provides a method of preventing, arresting progression of or ameliorating axonal injury characterized by overexpression of neurofilaments in a subject in need thereof.

In another aspect, the invention provides a method of preventing X-linked retinitis pigmentosa (XLRP) in a subject at risk of developing said disease. Subjects at risk of developing XLRP include those with a family history of XLRP, those with one or more confirmed mutations in the RPGR gene, offspring of female carriers of an RPGR mutation (heterozygous females), offspring of females carrying an RPGR mutation on both X chromosomes.

In another aspect, the invention provides a method of preventing, arresting progression of or ameliorating rod and/or R/G cone opsin mislocalization in a subject in need thereof. In normal eye, rhodopsin and R/G cone opsin are found predominantly in membranes of the rod cell outer segment but become mislocalized to the inner segment, ONL and/or the synaptic terminals in many retinal diseases and injuries, including XLRP.

In another aspect, the invention provides a method of preventing, arresting or ameliorating the increase in phagocytic cells in the subretinal space at later stages of the disease. See, Beltran et al, IOVS (2006) 47:1669-81, incorporated herein by reference herein.

In another aspect, the invention provides a method of preventing, arresting progression of or ameliorating OPL synaptic changes, bipolar cell abnormalities or inner retinal abnormalities associated with XLRP in a subject in need thereof. OPL synaptic changes include narrowing of the OPL associated with compressed photoreceptor synaptic terminals, and a reduction of the number of CtBP2-labeled synaptic ribbons in rod and cone terminals. Bipolar cell abnormalities include retraction of bipolar cell dendrites. Inner retinal abnormalities include inner retinal hyperthickness, rod photoreceptor neurite sprouting, rod bipolar cell dendrite retraction, increased GABA-immunoreactive amacrine cells, and changes in Müller glial cell reactivity, flattening of the axonal arborization of horizontal cells that can be labeled with a calbindin antibody; thinning and loss of lamination (at later stages of disease) of the inner plexiform layer (IPL) that can be tabled with GABA antibody. See, Beltran et al, IOVS, 2006, cited above and Aleman et al, IOVS (2007) 48:4759-65 incorporated by reference herein.

For each of the described methods, the treatment may be used to prevent the occurrence of retinal damage or to rescue eyes having mild or advanced disease. As used herein, the term "rescue" means to prevent progression of the disease to total blindness, prevent spread of damage to uninjured photoreceptor cells or to improve damage in injured photoreceptor cells. Thus, in one embodiment, the composition is administered before disease onset. In another embodiment, the composition is administered after the initiation of opsin mislocalization. In another embodiment, the composition is administered prior to the initiation of photoreceptor loss. In another embodiment, the composition is administered after initiation of photoreceptor loss. In yet another embodiment, the composition is administered when less than 90% of the photoreceptors are functioning or remaining, as compared to a non-diseased eye. In another embodiment, the composition is administered when less than 80% of the photoreceptors are functioning or remaining. In another embodiment, the composition is administered when less than 70% of the photoreceptors are functioning or remaining. In another embodiment, the composition is administered when less than 60% of the photoreceptors are functioning or remaining. In another embodiment, the composition is administered when less than 50% of the photoreceptors are functioning or remaining. In another embodiment, the composition is administered when less than 40% of the photoreceptors are functioning or remaining. In another embodiment, the composition is administered when less than 30% of the photoreceptors are functioning or remaining. In another embodiment, the composition is administered when less than 20% of the photoreceptors are functioning or remaining. In another embodiment, the composition is administered when less than 10% of the photoreceptors are functioning or remaining. In one embodiment, the composition is administered only to one or more regions of the eye, e.g., those which have retained photoreceptors. In another embodiment, the composition is administered to the entire eye.

In another embodiment, a method of treating or preventing XLRP in a subject in need thereof is provided. The method includes identifying a subject having, or at risk of developing, XLRP; performing genotypic analysis and identifying at least one mutation in the RPGR gene; performing non-invasive retinal imaging and functional studies and identifying areas of retained photoreceptors to be targeted for therapy; and administering to the subject an effective concentration of a composition, whereby XLRP is prevented, arrested or ameliorated. The composition includes a recombinant virus carrying a nucleic acid sequence encoding a normal photoreceptor cell-specific gene under the control of a promoter sequence which expresses the product of the gene in the photoreceptor cells, and a pharmaceutically acceptable carrier. Genotypic analysis is routine in the art and may include the use of PCR to identify one or more mutations in the nucleic acid sequence of the RPGR gene. See, e.g., Meindl et al, Nat Gen, May 1996, 13:35, Vervoort, R. et al, 2000. Nat Genet 25(4): 462-466 (cited above); and Vervoort, R. and Wright, A. F. 2002, Human Mutation 19: 486-500, each of which is incorporated herein by reference.

In another embodiment, any of the above methods are performed utilizing a composition comprising a recombinant AAV2/5 pseudotyped adeno-associated virus, carrying a nucleic acid sequence encoding a normal RPGR gene, or fragment thereof, under the control of an IRBP or GRK1 promoter which directs expression of the product of the gene in the photoreceptor cells of the subject, formulated with a carrier and additional components suitable for subretinal injection.

In another embodiment of the invention, the method includes performing functional and imaging studies to determine the efficacy of the treatment. These studies include ERG and in vivo retinal imaging, as described in the examples below. In addition visual field studies, perimetry, and microperimetry, mobility testing, visual acuity, color vision testing may be performed.

In yet another embodiment of the invention, any of the above described methods is performed in combination with another, or secondary, therapy. The therapy may be any now known, or as yet unknown, therapy which helps prevent, arrest or ameliorate XLRP or any of the above-described effects associated therewith. In one embodiment, the secondary therapy is Ciliary Neurotrophic Factor (CNTF). Sieving, P. A. et al, 2006. Proc Natl Acad Sci USA 103(10): 3896-3901, which is hereby incorporated by reference. The secondary therapy can be administered before, concurrent with, or after administration of the rAAV described above.

As is demonstrated in the examples below, an exemplary hRPGRORF15 was employed in in vivo experiments to provide evidence of the utility and efficacy of the methods and compositions of this invention. The examples demonstrated restoration of retinal function by the method of this invention in a large animal model of a human retinopathy. The use of the exemplary vector demonstrated in the experiments that the defect in the RPGR mutant dogs could be corrected by gene delivery. Retinal function was improved in this large animal model of blindness. This data allow one of skill in the art to readily anticipate that this method may be similarly used in treatment of XLRP or other types of retinal disease in other subjects, including humans.

F. Examples

EXAMPLE 1

Materials and Methods a. Human Subjects and Retinal Cross-Sectional Imaging

Patients with XLRP and molecularly confirmed RPGRORF15 mutations were included in this study. Informed consent was obtained. Procedures followed the Declaration of Helsinki guidelines and were approved by the institutional review board. Retinal cross-sectional imaging was obtained with spectral-domain optical coherence tomography (SD-OCT, RTVue-100; Optovue Inc., Fremont, Calif.). Recording and analysis techniques were published previously.

b. Animals

To define the structural and functional consequences of XLPRA1 and XLPRA2 disease and set the stage for treatment and outcome assessment, we used wild type (n-17, ages 7-416 wks), XLPRA1 (n=9, ages 7-156 wks) and XLPRA2 (n=6, ages 8-144 wks) dogs for non-invasive imaging and ERG studies. For gene therapy, crossbred affected dogs were used (Tables 1 & 2 below). All procedures involving animals were performed in compliance with the ARVO Statement for the Use of Animals in Ophthalmic and Vision Research and IACUC approval.

c. rAAV Vector Production and Purification

A full length human RPGRORF15 was cloned into AAV2/5 viral vectors and regulated by the human IRBP or GRK1 promoters. The vector cDNA was a full length human RPGRORF15 clone, based on the sequence published by Alan Wright and colleagues (BK005711) (http://www.ncbi.nlm.nih.gov/nuccore/BK005711), incorporated by reference herein. However, the sequence used in the construct (SEQ ID NO: 1) exhibits greater stability than the Wright sequence. This construct contains exons 1-ORF15, and was generated using 3-way ligation by step-wise amplifying exons 1-part of 15b (nucleotides 169-1990) from human lymphocytes and 1991-3627 from human genomic DNA. An internal restriction enzyme site NdeI (CATATG) was created by site-directed mutagenesis at residue 1993 (A>T). The RPGRORF15 sequence used in the constructs is shown in SEQ ID NO: 1. An alignment of the nucleic acid sequence published by Alan Wright and colleagues (BK005711) and SEQ ID NO: 1 is provided in FIGS. 3A-3E (See, also the aligned amino acid sequences encoded by the two nucleic acid sequences in FIGS. 4A and 4B, and a partial consensus sequence illustrated in FIG. 5). These fragments were then cloned in BamHI and XhoI sites in pBluescript, propagated in *E. coli* Stb14 and sequence-verified at the University of Michigan DNA sequencing core facility.

The human G-protein-coupled receptor protein kinase 1 (hGRK1) promoter was used to primarily control rod expression in the dog retina at a therapeutic concentration of $10^{11}$ vg/ml; higher concentrations ($10^{13}$) result in expression in some cones, but with adverse retinal effects. Expression in both rods and cones was regulated by 235 bp of the human IRBP promoter that contains the important cis-acting element identified in the mouse proximal promoter. See, al-Ubaidi M R, et al. (1992), J Cell Biol 119:1681-1687 and Boatright J H, et al. 1997) Mol Vis 3:15, both incorporated by reference herein. Vectors with this promoter result in GFP expression in both rods and cones in a dose and time dependent manner (FIG. S4 of Beltran 2012 which is reproduced as FIG. 8 of US Provisional Patent Application No. 61/670,355). Vector DNA sequences were confirmed for accuracy before vector production.

The two-plasmid co-transfection method was used to produce the AAV2/5 vector (See, Zolotukhin S, et al. (1999) Gene Ther 6:973-985 which is incorporated by reference herein). Viral particles were titered and resuspended in balanced salt solution (BSS, Alcon Laboratories, Fort Worth, Tex.) containing 0.014% Tween-20 at a concentration of $1.5 \times 10^{11}$ viral vector genomes per mL (vg/ml). Sterility and the lack of endotoxin were confirmed in the final product.

d. Subretinal Injections and Post Treatment Management

Subretinal injections were performed under general anesthesia as previously published (See, e.g., Beltran W A, et al. (2010) Gene Ther. 17:1162-1174 and Komaromy A M, et al. (2010) Hum Mol Genet 19:2581-2593, both incorporated by reference herein). The volume injected was dependent on age/eye size: 70 µl and 150 µl, respectively, at 5 and 28 wks of age, with the therapeutic vector injected in the right eye, and BSS injected in the left. At the time of the injection, the location and extent of the subretinal blebs were recorded on fundus photographs or schematic fundus illustrations; in all cases the blebs flattened and the retina reattached within 24 hrs. Failed subretinal injection that refluxed into the vitreous was found in one dog that was maintained throughout the study to determine potential therapeutic efficacy and/or ocular complications by the intravitreal route.

e. Clinical Assessment and In Vivo Retinal Imaging

Ophthalmic examinations were conducted throughout the injection-termination time interval. En face and retinal cross-sectional imaging was performed under general anesthesia, and retinal cross-sections with SD-OCT were analyzed as described (Aleman T S, et al. (2007) Invest Ophthalmol Vis Sci 48:4759-4765; Jacobson S G, et al. (2011) Invest Ophthalmol Vis Sci 52:70-79; Jacobson S G, et al. (2009) Invest Ophthalmol Vis Sci 50:1886-1894; Jacobson S G, et al. (2008) Invest Ophthalmol Vis Sci 49:4573-4577, all of which are incorporated by reference herein). En face and retinal cross-sectional imaging was performed with the dogs under general anesthesia. Overlapping en face images of reflectivity with near-infrared illumination (820 nm) obtained (HRA2 or Spectralis HRA or Spectralis HRA+ OCT, Heidelberg, Germany) with 30° and 55° diameter lenses to delineate fundus features such as optic nerve, retinal blood vessels, boundaries of injection blebs, retinotomy sites and other local changes. Custom programs (MatLab 6.5; The MathWorks, Natick, Mass.) were used to digitally stitch individual photos into a retina-wide panorama. In a subset of eyes, short-wavelength (488 nm) illumination was used to delineate the boundary of the tapetum and pigmented RPE. Spectral-domain optical coherence tomography (SD-OCT) was performed with linear and raster scans (RTVue-100, Optovue, Inc. Fremont, Calif. or Spectralis HRA+OCT, Heidelberg, Germany).

Linear scans were placed across regions or features of interest such as bleb boundaries in order to obtain highly resolved local retinal structure. The bulk of the cross-sectional retinal information was obtained from overlapping raster scans covering large regions of the retina. Either 6×6 mm (101 lines of 513 longitudinal reflectivity profiles (LRPs) each, no averaging, Optovue) or 9×6 (49 lines of 1536 LRPs each, averaging 8-10, Spectralis) was used.

Post-acquisition processing of OCT data was performed with custom programs (MatLab 6.5; The MathWorks, Natick, Mass.). For retina-wide topographic analysis, integrated backscatter intensity of each raster scan was used to locate its precise location and orientation relative to retinal features visible on the retina wide mosaic formed by NIR reflectance images. Individual LRPs forming all registered raster scans were allotted to regularly spaced bins (1°×1°) in a rectangular coordinate system centered at the optic nerve; LRPs in each bin were aligned and averaged. Intraretinal peaks and boundaries corresponding to histologically definable layers were segmented semi-automatically with manual override using both intensity and slope information of backscatter signal along each LRP. Specifically, the retina-vitreous interface, OPL, outer limiting membrane (OLM), signal peak near the inner/outer segment (IS/OS) junction, and the RPE were defined. In the superior retina of the dog, backscatter from the tapetum forms the highest intensity peak, and RPE and IS/OS peaks are located vitreal to the tapetal peak. ONL thickness was defined from the sclerad transition of the OPL to the OLM, and ONL thickness topography was calculated. In addition, the topography of IS/OS backscatter intensity was calculated by first measuring the mean backscatter intensity within ±8 µm of the IS/OS peak and then normalizing this value by the mean backscatter intensity of the first 75 µm of retina sclerad to the retina-vitreous interface. For all topographic results, locations of blood vessels, optic nerve head and bleb boundaries were overlaid for reference. Further quantitative comparisons were achieved by sampling the ONL thickness of a 10° wide band along the vertical meridian crossing the optic nerve head.

f. Electroretinography

Dogs were dark-adapted overnight, premedicated, and anesthetized as described (Acland G M, et al. (2001) Nature Genetics 28:92-95; Kijas J W, et al, (2002) Proc Natl Acad Sci USA 99:6328-6333, both of which are incorporated by reference herein). Pupils were dilated with atropine (1%), tropicamide (1%) and phenylephrine (10%). Pulse rate, oxygen saturation, and temperature were monitored. Full-field ERGs were recorded with Burian-Allen (Hansen Ophthalmics, Iowa City, Iowa) contact lens electrodes and a computer-based system. White flashes of low-energy (10 µs duration; 0.4 log scot-cd.s.m-2) and high-energy (1 ms duration; 3.7 log scot-cd.s.m-2) were used under dark-adapted and light-adapted (1.5 log cd.m-2 at 1 Hz stimulation, 0.8 log cd.m-2 at 29 Hz stimulation) conditions. Leading edges of high-energy flash responses were measured at the fixed time point of 4 ms (Acland G M, et al. (2005) Mol Ther 12:1072-1082, incorporated by reference herein) to quantify retinal function dominated by the rod photoreceptors and the peak-to-peak amplitude of the low-energy flashes at 29 Hz were measured to quantify retinal function dominated by the cone photoreceptors. Assessment of visual behavior using qualitative or quantitative measures was not performed in treated animals because, at the disease stages studied, both mutant strains (untreated) retain sufficient rod and cone visual function that they are not distinguishable from normal.

g. Tissue Processing and Morphologic Assessment

Dogs were euthanatized by intravenous injection of euthanasia solution (Euthasol, Virbac, Ft. Worth, Tex.), and the globes enucleated, fixed and processed as previously described (Beltran W A et al, (2006) Invest Ophthalmol Vis Sci 47:1669-1681, incorporated by reference herein). Serial 10 µm thick retinal cryosections that encompassed treated and non-treated regions were cut (~700/retina), and a subset stained with H&E; vascular landmarks were used to place the section on the en face cSLO images and subsequent en face ONL maps. Immunohistochemistry was done in adjacent sections with antibodies directed against rod opsin, human cone arrestin (LUMIf; 1/10 000 provided by Cheryl Craft), R/G-opsin, RIBEYE/CtBP2, PKCα, Goα, calbindin, neurofilament (NF200 kDa), and GFAP to examine the expression of molecular markers in treated and non-treated areas (Beltran W A et al (2006), cited above, and Beltran W A et al (2009) Invest Ophthalmol Vis Sci 50:3985-)995, each of which is incorporated by reference herein). As well, an antibody directed at the C-terminal domain of human RPGR (Khanna H, et al. (2005) J Biol Chem 280:33580-33587, incorporated by reference herein) was used to identify the therapeutic transgene in treated eyes. The antigen-antibody complexes were visualized with fluorochrome-labeled secondary antibodies (Alexa Fluor, 1:200; Molecular Probes, Eugene, Oreg., USA) with DAPI to label cell nuclei, and digital images taken (Spot 4.0 camera, Diagnostic Instruments, Sterling Heights, Mich.), and imported into a graphics program (Photoshop; Adobe, Mountain View, Calif., USA) for display.

EXAMPLE 2

RPGR ORF15 Mutations Lead to Photorecepto Egeneration in Humans and Dogs

Topography of photoreceptors can be mapped across the retina of patients with RPGR-XLRP by measuring the thickness of the outer (photoreceptor) nuclear layer (ONL) using cross-sectional OCT retinal imaging. As shown in FIG. 1A of Beltran Wash., et al, (2012 January) Proc Natl Acad Sci USA, 109(6):2132-7 (Beltran 2012), which is reproduced as FIG. 1A of U.S. Provisional Patent Application No. 61/670,355, in normal eyes (inset), ONL thickness peaks centrally and declines with distance from the fovea. XERP patients with ORF15 mutations can have different disease patterns. A common pattern shows dramatic photoreceptor losses with relatively greater retention of ONL thickness at and near the cone-rich foveal region surrounded by a zone of detectable but markedly thinned ONL (FIG. 1A of Beltran 2012 which is reproduced as FIG. 1A of U.S. Provisional Patent Application No. 61/670,355). RPGR disease expression also includes the less common phenotype characterized by loss of central photoreceptors and diseased, yet better preserved, peripheral photoreceptors (FIG. 1A of Beltran 2012 which is reproduced as FIG. 1A of U.S. Provisional Patent Application No. 61/670,355). The present examples, taken together with previous observations, demonstrate there can be a spectrum of human RPGR-XLRP phenotypes. Most of the phenotypes have rod more than cone dysfunction by ERG.

The two canine models can also be studied with cross-sectional retinal imaging, such as we used for human patients, and topographical photoreceptor maps generated and compared with normal data (FIG. 1B of Beltran 2012 which is reproduced as FIG. 1B of U.S. Provisional Patent Application No. 61/670,355). Of translational importance, a spectrum of disease patterns also occurs in the canine models. XLPRA1 dogs, for example, can show ONL thinning with relative preservation of a region immediately superior to the optic nerve, corresponding to the high photoreceptor density of the visual streak. In contrast, an example of an XLPRA2 photoreceptor map shows a pattern of retina-wide ONL thinning, but more pronounced losses in the central retina, corresponding to the visual streak, than in peripheral retina.

The natural history of photoreceptor degeneration was determined to select the age and retinal site for treatment in XLPRA1 and XLPRA2 (FIG. 1C of Beltran 2012 which is reproduced as FIG. 1C of U.S. Provisional Patent Application No. 61/670,355). Spatio-temporal distribution of photoreceptor degeneration and the disease course were determined by quantifying ONL thickness along the vertical meridian (FIG. 1C of Beltran 2012 which is reproduced as FIG. 1C of U.S. Provisional Patent Application No. 61/670,355). Wild type dogs (WT) (n=5, ages 7-43 wks) show a relatively uniform ONL thickness with slightly higher values (averaging 57 µm) superior to the optic nerve up to eccentricities of 35°, and slightly lower values (averaging 54 µm) inferior to the optic nerve up to 25°, XLPRA1 at younger ages (n=7, ages 7-28 wks) shows ONL thickness that is within or near normal limits (FIG. 1C of Beltran 2012 which is reproduced as FIG. 1C of U.S. Provisional Patent Application No. 61/670,355). Older XLPRA1 (n=6, ages 56-76 wks) shows ONL thinning in the inferior retina and relative preservation of the visual streak region immediately superior to the optic nerve (FIG. 1C, brackets, of Beltran 2012 which is reproduced as FIG. 1C of U.S. Provisional Patent Application No. 61/670,355). There can be greater differences among older XLPRA1 eyes, with some results near the lower limit of normal and others showing substantial ONL loss below 50% of WT (FIG. 1C of Beltran 2012 which is reproduced as FIG. 1C of U.S. Provisional Patent Application No. 61/670,355), consistent with variable severity of disease as previously reported.

XLPRA2 at the youngest ages examined (n=2, ages 8, 22 wks), we observed retina-wide ONL thinning that tended to be greater in the central retina (44% of WT), corresponding to the visual streak, than in the periphery (60% of WT) (FIG. 1C of Beltran 2012 which is reproduced as FIG. 1C of U.S. Provisional Patent Application No. 61/670,355). Older XLPRA2 dogs (n=3, ages 36-59 wks) show more ONL thinning with a tendency for greater central and inferior retinal disease (30% of WT) than in the superior peripheral retina (45% of WT) (FIG. 1C of Beltran 2012 which is reproduced as FIG. 1C of U.S. Provisional Patent Application No. 61/670,355). ONL thickness in the oldest XLPRA1 and XLPRA2 eyes was substantially reduced (FIG. 1C of Beltran 2012 which is reproduced as FIG. 1C of U.S. Provisional Patent Application No. 61/670,355). Rod and cone retinal function in young and older dogs with XLPRA1 and. XLPRA2 was measured by ERG. Both XLPRA1 and XLPRA2 diseases could be characterized as having more rod than cone dysfunction. Younger XLPRA1 eyes (n=6) showed abnormal (4/6) rod function but normal cone function (FIG. 1D of Beltran 2012 which is reproduced as FIG. 1D of U.S. Provisional Patent Application No. 61/670,355) whereas older XLPRA1 eyes (n=7) showed abnormal rods (6/7) and cones (5/7) (FIG. 1D of Beltran 2012 which is reproduced as FIG. 1D of U.S. Provisional Patent Application No. 61/670,355). Younger XLPRA2 eyes (n=3) had abnormal rod function but mostly (2/3) normal cone function, but older XLPRA2 eyes (n=6) had abnormal rod and cone function (FIG. 1D of Beltran 2012 which is reproduced as FIG. 1D of U.S. Provisional Patent Application No. 61/670,355). Defining the differences in structural and functional natural history of XLPRA1 and XLPRA2 diseases showed a sufficient overlap in the non-invasive studies in dog and man to validate the use of the dog models in proof-of-concept studies of treatment that may be relevant to RPGR-XLRP patients.

EXAMPLE 3

Treatment of XLPRA with Gene Knockdown and Replacement Strategy—in vivo Findings It was hypothesized that a gene knockdown and replacement strategy would be necessary in order to overcome the effects of the mutated RPGR gene. Thus, a short hairpin RNA was encoded into a construct containing a canine shortened RPGRORF15 cDNA, which has had 708 bp removed in frame from the repetitive region of ORF15 (cRPGR$_{short}$). Additional silent mutations were included in the cRPGR sequence to "harden" the sequence to the siRNA.

Subretinal injection of the cRPGR$_{short}$ cDNA under the control of hIRBP promoter (AAV2/5-hIRBP-cRPGR$_{short}$-shRNA5) was performed m XLPRA2 dogs. Treatment was initiated at 5 weeks, after disease onset. Severe retinal lesions of retinal dysplasia were observed at 17 weeks following sub-retinal injection. No rescue was seen (Table 2).

EXAMPLE 4

Treatment of XLPRA with Gene Augmentation Therapy—in vivo Findings

Figure 2:
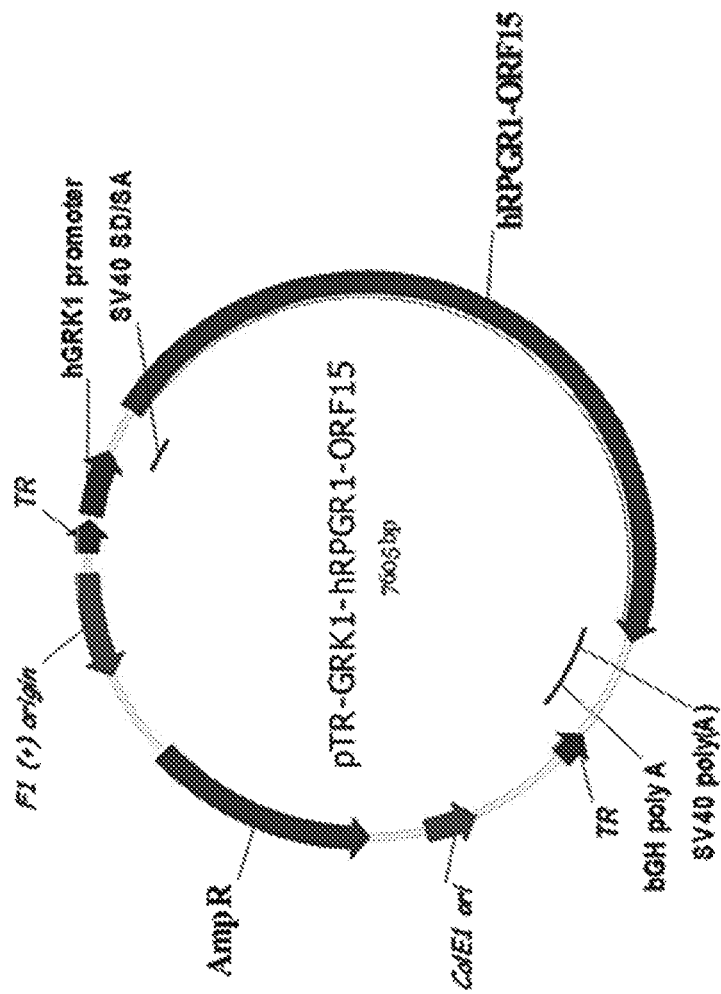
FIG. 2 is a plasmid map of the AAV2/5 vector incorporating the hGRK1 promoter (SEQ ID NO: 3) and hRPGR1-ORF15 gene.

Subretinal injection of the full-length human RPGRORF15 cDNA under control of hIRBP (AAV2/5-hIRBP-hRPGR) (FIG. 1) promoter was performed in both XERPA1 and XLPRA2, and under control of hGRK1 (AAV2/5-hGRK1-hRPGR) (FIG. 2) promoter in XLPRA2 (Table 1). In XLPA1, treatment was initiated at 28 wks, before photoreceptor loss, and monitored to 77 wks, well after the start of degeneration (FIG. 1C of Beltran 2012 which is reproduced as FIG. 1C of U.S. Provisional Patent Application No. 61/670,355). In XLPRA2, the injections were performed at 5 wks of age, and the study terminated at 38 wks. In contrast to the treatment failures discussed above, the full length human RPGRORF15 (driven by hIRBP or hGRK1 promoters) was therapeutically effective, As shown in FIG. S5 of Beltran 2012, which is reproduced as FIG. 9 of U.S. Provisional Patent Application No. 61/670,355) demonstrates that AAV2/5 vector with hIRBP promoter targets expression to rods and cones. This figure shows native GFP fluorescence (green) in normal canine retina 2 and 8 wks following subretinal injection of AAV2/5-hIRBP-hGFP. 150 µl injections of 2 vector titers were used. GFP fluorescence in photoreceptors is present by 2 wks (A1, A2), and is increased at 8 wks (B1, B2). Expression is found in both rods and cones as confirmed by colocalization with cone arrestin in retinas treated with lower vector doses which result in fewer cones transduced (C). More photoreceptors are labeled at the higher dose, and expression is sustained during 8 week treatment period.

The positive treatment response was detectable in vivo. Treated eyes of XLPRA1 dogs had thicker ONL in the superior peripheral retina, specifically on the treated side of the subretinal injection area (bleb) boundary compared to the untreated side (FIG. 2A of Beltran 2012 which is reproduced as FIG. 2A of U.S. Provisional Patent Application No. 61/670,355). Additionally, the signal peak corresponding to the region of photoreceptor inner and outer segments (IS/OS) was more intense and better organized on the treated side (FIG. 2A of Beltran 2012 which is reproduced as FIG. 2A of U.S. Provisional Patent Application No. 61/670,355). Treated eyes of XLPRA2 dogs showed thicker ONL on the treated side or higher intensity signal at the level of the IS/OS (FIG. 2A of Beltran 2012 which is reproduced as FIG. 2A of U.S. Provisional Patent Application No. 61/670,355). To understand better the relationship between the treatment bleb and local retinal structure, ONL thickness was mapped across wide expanses of the treated and control eyes (FIG. 2B of Beltran 2012 which is reproduced as FIG. 2B of U.S. Provisional Patent Application No. 61/670,355). XLPRA1 dog H484 at 76 weeks of age had a clearly demarcated zone of ONL retention within the treatment bleb in superior peripheral retina (FIG. 2B of Beltran 2012 which is reproduced as FIG. 2B of U.S. Provisional Patent Application No. 61/670,355). There was ONL degeneration outside the bleb in the superior temporal retina. In the central retinal region where XLPRA1 dogs at this age retain near normal ONL thickness (FIG. 1C of Beltran 2012 which is reproduced as FIG. 1C of U.S. Provisional Patent Application No. 61/670,355)), a transition across the bleb boundary was less detectable (FIG. 2B of Beltran 2012 which is reproduced as FIG. 2B of U.S. Provisional Patent Application No. 61/670,355)).

XLPRA1 dog H483 with a smaller subretinal bleb had similar findings in the superior peripheral region with local evidence of ONL thickness retention inside the bleb boundary. More centrally, both treated and untreated regions retained near normal ONL thickness and there was no change in ONL thickness corresponding to the bleb boundary (FIG. 2B of Beltran 2012 which is reproduced as FIG. 2B of U.S. Provisional Patent Application No. 61/670,355). XLPRA1 dog Z412 showed a region with preserved ONL that corresponded to the bleb boundary; ONL was abnormally thinned outside this boundary (FIG. 2B of Beltran 2012 which is reproduced as FIG. 2B of U.S. Provisional Patent Application No. 61/670,355). Longitudinal follow-up from 21 to 36 wks showed the time course of ONL degeneration outside the bleb of the treated eye and in the BSS-injected control eye (FIG. S1 of Beltran 2012 which is reproduced as FIG. 5 of U.S. Provisional Patent Application No. 61/670,355). XLPFA2 dog Z414 showed a region of slight ONL thickness retention approximately corresponding to the bleb boundary (FIG.2B of Beltran 2012 which is reproduced as FIG. 2B of U.S. Provisional Patent Application No. 61/670,355).

Changes at the level of photoreceptor IS/OS were quantified. Backscatter intensity at this layer was segmented and mapped (FIG. 2C of Beltran 2012 which is reproduced as FIG. 2C of U.S. Provisional Patent Application No. 61/670,355). IS/OS intensity maps of three of the treated dogs (H484, H483 and Z412) were similar to the ONL maps, such that regions of retained ONL corresponded to higher intensity. In the case of Z414, the treated region showed substantially higher backscatter intensity at the IS/OS layer and this was consistent with the better layer definition apparent in individual scans (FIG. 2A of Beltran 2012 which is reproduced as FIG. 2A of U.S. Provisional Patent Application No. 61/670,355). Comparison of the treated and BSS-injected control eyes showed the clearly delineated retinal regions with treatment-related effects (FIG. 2C, hashed, of Beltran 2012 which is reproduced as FIG. 2C of U.S. Provisional Patent Application No. 61/670,355). ERGs were evaluated in terms of interocular asymmetry (FIG. 2D of Beltran 2012 which is reproduced as FIG. 2D of U.S. Provisional Patent Application No. 61/670,355). Signals were larger in the treated eyes of three dogs (H484, Z412 and Z414) for photoreceptor responses dominated by rods, and for post-receptoral bipolar cell responses mediated by both rods and cones. H483 had the least degenerate retina and normal amplitude responses bilaterally (FIGS. 2D and S2 of Beltran 2012 which is reproduced as FIGS. 2D and 6 of U.S. Provisional Patent Application No. 61/670,355) that were symmetric for cones and asymmetric for rods, favoring the untreated eye.

These data are summarized in Tables 1 and 2 below:

TABLE 1

| Genotype Animal/ eye | Age (wks)[1] | | Agent Injected | OCT | | ERG[5] | | Morphology/ IHC | | Inner Retina[8] | hRPGR Exp[9] |
|---|---|---|---|---|---|---|---|---|---|---|---|
| | Begin | End | | ONL[3] | IS/OS[4] | Rod | Cone | PR[6] | OPL[7] | | |
| XLPRA1 H484-RE | 28 | 77 | hIRBP-hRPGR | + | + | + | + | N | N | N | +3 |
| XLPRA1 H484-LE | 28 | 77 | BSS | − | − | + | + | D | D | D | − |
| XLPRA1 H483-RE | 28 | 77 | hIRBP-hRPGR | + | + | − | − | N | N | N | +2 |
| XLPRA1 H483-LE | 28 | 77 | BSS | − | − | − | − | D | D | D | − |
| XLPRA2 Z412-RE | 5 | 38 | hIRBP-hRPG | + | + | + | + | N | N | N | +2 |
| XLPRA2 Z412-LE | 5 | 38 | BSS | − | − | + | + | D | D | D | − |
| XLPRA2 Z414-RE | 5 | 38 | hGRK1-hRPGR | − | + | + | + | P | P | P | +1 |
| XLPRA2 Z414-LE | 5 | 38 | BSS | − | − | + | + | D | D | D | − |
| XLPRA2 Z413-RE | 5 | 38 | hGRK1-hRPGR[10] | ND | ND | ND | ND | D | D | D | − |

NOTES:
BSS—balanced salt solution;
RE—right eye;
LE—left eye;
ND—not done.
[1]The span of ages (in weeks) from treatment to termination.
[2]Subretinal injections with a volume of 70 μl at 5 wks of age, and 150 μl at 28 wks. AAV2/5 vector injections had a titer of 1.5 × 10[11] vg/ml. Dog Z413 had 70 μl injected into the vitreous and served as control.
[3]Existence of a region of retained outer nuclear layer (ONL) within the injection bleb compared to outside the bleb as measured by optical coherence tomography (OCT); + = positive treatment outcome, − = no response to treatment.
[4]Existence of a region of higher inner segment/outer segment (IS/OS) reflectivity within the injection bleb compared to outside the bleb as measured by OCT; + = positive treatment outcome, − = no response to treatment.
[5]Interocular asymmetry of the rod- or cone-dominated electroretinogram (ERG) amplitudes
[6]Photoreceptors (PR). Structure of rods, cones and outer nuclear layer in treated vs untreated regions, and reversal of rod and cone opsin mislocalization. N = normal, rescue; D = diseased, no rescue; P = partial rescue.
[7]Outer plexiform layer (OPL), Pre- and post-synaptic terminal structures, including presence of normal elongated bipolar dendrites as determined by immunohistochemistry (IHC) using antibodies that label photoreceptor synaptic terminals and bipolar cells. N = normal, rescue; D = diseased, no rescue; P = partial rescue.
[8]Reversal/prevention of inner retinal remodeling. N = normal, rescue; D = diseased, no rescue; P = partial rescue.
[9]hRPGR expression in treated area determined with a C-terminal antibody. Labeling limited to rods and cones and graded as − (no label), +1 (weak), +2 (moderate), and +3 (intense).
[10]Represents an intra vitreal control.

TABLE 2

| Animal/ Process | Age (wks) Begin/ End | Promoter-transgene (# of eyes) | Vector titer (vg/ml) | Outcome Rescue | Complications |
|---|---|---|---|---|---|
| XLPRA1/ Augmentation | 26-28/ 31-37 | mOP-cRPGR (1) | $1.5 \times 10^{11}$ | No | Multifocal rosettes (1) |
| | | hIRBP-HiscRPGR (4) | $1.5 \times 10^{11}$ | No | Multifocal rosettes (4) |
| | | hGRK1-hRPGR (1) | $1.5 \times 10^{11}$ | ** | Small retinal detachments (1) |
| XLPRA2/ Knockdown | 5-22/ 20-39 | CBA-GFP-H1-siRNA3 (1) | 2.8-$2.9 \times 10^{11}$ | No | None |
| | | CBA-GFP-H1-siRNA5 (1) | | No | None |
| | | CBA-GFP-H1-siRNA5 (1) | | No | None |
| | | CBA-GFP-H1-siRNA5 (2) | | No | None |
| XLPRA2/ Knockdown + Augmentation | 5/22 | hIRBP-cRPGR_HT-H1-siRNA5 (3) | $1.5 \times 10^{10}$-$1.5 \times 10^{11}$ | No | Multifocal rosettes (2) None (1) |
| | | hIRB-cRPGR_HT-H1-siRNA5 (2)-IV | $1.5 \times 10^{10}$-$1.5 \times 10^{11}$ | No | None (2) |

NOTES:
c = canine; h = human; IV—intravitreal control; mOP = minimal opsin promoter; CBA = chicken beta actin promoter[65].
** Mild and non-uniform hRPGR expression in treatment area, partial recovery of opsin mislocalization. Photoreceptor rescue was not interpretable because of the retinal detachments, and early termination secondary to these complications.

Previous hypotheses about XLPRA2 being due to a toxic gain of function[63] led to attempts to downregulate mutant RPGR expression in order to improve the disease. Two KD reagents, shRNA3 and shRNA 5, were used that were effective downregulating canine RPGR expression in vitro but there was no rescue. Simultaneous replacement of RPGR used a single viral construct that combined shRNA5 and a resistant abbreviated[64] canine RPGR cDNA that had a 5' 6xHis tag. Subretinal treatment with high vector titer resulted in no efficacy and retinal toxicity. Similar retinal toxicity was observed by augmentation alone with the abbreviated canine RPGR cDNA without the His tag.

EXAMPLE 5

Gene Augmentation Rescues Photoreceptors and Reverses Mislocalization of Rod and Cone Opsins in Both XLPRA Genotypes Assessment of retinal morphology in tissue sections that included the bleb boundary confirmed the in vivo imaging results of retention of ONL thickness and photoreceptor preservation in subretinally-treated areas (Panels 1-5 in FIGS. 3 and S3 of Beltran 2012 which are reproduced as FIGS. 3 and 7 of U.S. Provisional Patent Application No. 61/670,355). Intravitreal vector administration was comparable to no treatment (Table 1). In the three dogs treated with AAV2/5-hIRBP-hRPGR (H484, H483, Z412) rod and cone IS and OS structure was normal within the bleb boundary. In the untreated areas, IS were short and OS sparse and irregular (Panels 3, 4 in FIGS. 3 and S3 of Beltran 2012 which are reproduced as FIGS. 3 and 7 of U.S. Provisional Patent Application No. 61/670,355). In Z414, treated with AAV2/5-hGRK1-hRPGR, a milder yet positive photoreceptor rescue was observed in the bleb area (FIG. S3C of Beltran 2012 which is reproduced as FIG. 7C of U.S. Provisional Patent Application No. 61/670,355). Immunolabeling with an antibody directed against human RPGRORF15 detected robust hRPGR protein expression limited to photoreceptors in the treatment area (Table 1). Labeling was found throughout the IS and synaptic terminals in the four dogs, as well as the rod and cone perinuclear region of H484 (Panels 6-8 in FIGS. 3 and S3 of Beltran 2012 which are reproduced as FIGS. 3 and 7 of U.S. Provisional Patent Application No. 61/670,355). Finally, the mislocalization of rod and cone opsins, a feature of the disease in human, mouse and dog, was reversed. (Panels 9,10,12,13 in FIGS. 3 and S3 of Beltran 2012 which are reproduced as FIGS. 3 and 7 of U.S. Provisional Patent Application No. 61/670,355) in the three dogs treated with AAV2/5-hIRBP-hRPGR. Reduced yet distinct rod and R/G cone opsin mislocalization was apparent in Z414, treated with AAV2/5-hGRK1-hRPGR (FIG. S3C of Beltran 2012 which is reproduced as FIG. 7C of U.S. Provisional Patent Application No. 61/670,355).

EXAMPLE 6

Prevention of Secondary OPL, Bipolar Cell and Inner Retinal Disease

In XLPRA, like other primary photoreceptor diseases, OPL and inner retinal abnormalities are common secondary effects. In untreated regions, narrowing of the OPL was associated with compressed photoreceptor synaptic terminals (Panels 2, 5 in FIGS. 3 and S3 of Beltran 2012 which are reproduced as FIGS. 3 and 7 of U.S. Provisional Patent Application No. 61/670,355), and a reduction of the number of CABP2-labeled synaptic ribbons in rod and cone terminals (Panels 1, 2 in FIGS. 4 and S4 of Beltran 2012 which are reproduced as FIGS. 4 and 8 of U.S. Provisional Patent Application No. 61/670,355). In parallel, rod and cone bipolar cell dendrites retracted (Panels 3, 4 in FIGS. 4 and S4 of Beltran 2012 which are reproduced as FIGS. 4 and 8 of U.S. Provisional Patent Application No. 61/670,355). These secondary changes were absent in treated areas, resulting in a preserved OPL. In contrast, calbindin labeling of horizontal and amacrine cells (Panels 5, 6 in FIGS. 4 and S4 of Beltran 2012 which are reproduced as FIGS. 4 and 8 of U.S. Provisional Patent Application No. 61/670,355), and their lateral processes, was normal and unchanged between treated and untreated regions. These hallmarks of late stage retinal remodeling in XLPRA were not expected to be present at the age when dogs were terminated.

The dendritic terminals of horizontal cells, as well as that of ganglion cells, and the nerve fiber layer of treated and untreated regions appeared normal when labeled with an antibody directed against the neurofilament heavy chain (NF 200 kDa). However, there was punctate NF200 staining in the ONL. Overexpression of neurofilaments is a characteristic of axonal injury in several neurodegenerative disorders, and occurs in this and other retinal diseases. This finding was restricted to the untreated regions of all dogs, and was absent or reduced in treated areas (Panels 5, 6 in FIGS. 4 and S4 of Beltran 2012 which are reproduced as FIGS. 4 and 8 of U.S. Provisional Patent Application No. 61/670,355). GFAP immunolabeling clearly delineated untreated regions that showed increased Müller glia reactivity, whereas it diminished in the transition zone between treated and untreated regions, and was absent in the bleb area (Panels 7, 8 in FIGS. 4 and S4 of Beltran 2012 which are reproduced as FIGS. 4 and 8 of U.S. Provisional Patent Application No. 61/670, 355). In summary, inner retinal rescue was complete in 3 of 4 treated eyes; rescue was partial for the one treated with AAV2/5-hGRK1-hRPGR where rod neurite sprouting extended into the inner retina (Table 1), and NF200 labeling pattern was intermediate between normal and disease (FIG. S4D of Beltran 2012 which is reproduced as FIG. 8D of U.S. Provisional Patent Application No. 61/670,355). The results clearly show that targeting RPGR augmentation to photoreceptors in both XLPPA1 and XLPRA2 corrects the primary photoreceptor defect, and has beneficial downstream effects OPL and inner retinal abnormalities are prevented or reversed.

EXAMPLE 7

Discussion

Recent successes using gene replacement to treat LCA2, the autosomal recessive RPE disease due to RPE65 mutations, have paved the way for considering gene therapy for treating other incurable human retinopathies. XLRP is among candidate diseases for treatment because it can be identified in the clinic, either through pedigree analysis, carrier identification or by the fact that there is a high frequency of XLRP among simplex males with RP; and mutations in RPGRORF15 account for about 75% of XLRP patients. The current results showing treatment efficacy in two large animal models of human RPGRORF15-XLRP strongly suggest that a gene augmentation strategy is a viable option for this photoreceptor ciliopathy, and complements successful rod rescue in a murine model of the Bardet-Biedl syndrome ciliopathy.

The disease in humans and in animal models is not, however, without complexity and future therapy of the human disease will need to be approached with caution. For example, there are modifiers that may affect disease expression in both patients and dog models, and there is a spectrum of phenotypes between and within RPGRXLRP families and in the dog XLPRA1 model. The phenotypic diversity may be a potential obstacle to patient selection, and points to the need for more than a molecular diagnosis and patient's age as criteria to determine candidacy for treatment. In support of genotype data there must be complementing detailed non-invasive retinal imaging and function studies. The temptation should be resisted in early human treatment approaches to try to design a treatment to fit all phenotypes and all disease stages. The dog diseases are mainly rod>cone degenerations, and there was efficacy in treating both the severe XLPRA2 with central retinal degeneration, and the less severe XLPRA1 with central retinal preservation using vectors that targeted both rods and cones. Not included in the canine disease spectrum, however, are certain human RPGR-XLRP phenotypes, such as mild cone>rod or cone dystrophies. Some patients can show very limited or even normal rod function, and cone targeting strategies must be developed for these subtypes. Proof-of-principle studies targeting cone diseases already have been successful in both mouse and dog models with mutations in cone phototransduction or cyclic GMP channel genes, so translation to the clinic would be expedited.

The reported intrafamilial variation of phenotypes neither excludes nor includes entire pedigrees from participation, but further strengthens the case for complete clarification of phenotype in individual patients. Furthermore, in the present study, there was no attempt to target the very central retina; the extracentral subretinal approach as used in the dogs would be the advisable strategy for early phase human clinical trials based on the current observations. However, many RPGR patients show continued survival of foveal cones and impaired but useful visual acuity in late disease stages. As subfoveal injections of vector-gene have been shown to cause loss of diseased foveal cones, alternate means of therapeutic gene delivery should be considered. Advances in intravitreal delivery systems to treat the outer retina, e.g. using mutant AAV capsid vectors, eventually could allay the safety concerns in treating residual foveal cones.

While it is clear that RPGR-associated disease is common and generally severe, the function of the gene, and the association between mutation and disease are less well understood. RPGR has a complex splicing pattern with multiple tissue-/cell-specific isoforms, is known to interact with a number of ciliary proteins, acts as a gunanine nucleotide exchange factor for small GTPase RAB8A and may have a role in vertebrate development. Such complexity may account partially for the variability in disease phenotype. In general, loss of function or gain of function mechanisms have been proposed, a suggestion that each would require different therapeutic approaches. Although our present studies cannot rule out either mechanism as causal to disease, the results clearly indicate that gene augmentation alone is effective in preventing disease, or arresting progression of and reversing the degenerative process in canine models of ORF15 mutations. These fundamental findings allow us to move forward therapeutically towards translational studies while the specific disease mechanisms await further elucidation.

Our results emphasize that targeting therapy to rod and cone photoreceptors is essential for functional and structural rescue in RPGR-associated retinal disease. The hIRBP promoter that regulates expression of the therapeutic gene results in robust expression of reporter or therapeutic genes in both cell types (FIG. S5 and Panels 6-8 in FIGS. 3 and S3 of Beltran 2012 which are reproduced as FIGS. 9, 2 and 7, respectively, of U.S. Provisional Patent Application No. 61/670,355), and expression is sustained. As IRBP also is expressed in human cones, we expect efficient targeting of rods and cones with this promoter in future translational studies. When regulated by the hGRK1 promoter, the therapeutic transgene expression was low in rods, and to a lesser extent in cones. Remaining photoreceptor structure, albeit abnormal, was considerably improved over untreated regions. However, because GRK1 is expressed in human cones, we expect targeting efficiency of GRK to be increased in humans. See, e.g., Weiss, E. R. et al, 2001. J Neurosei 21(23): 9175-9184, which is hereby incorporated by reference.

In XLPRA1, treatment before disease onset prevented disease development. Further, treatment of XLPRA2 after disease onset, and whilst photoreceptor cell death was ongoing (at 5 wks cell death is ~50% of the maximal rate determined by TUNEL labeling), arrested progression of the disease, and the morphology of the remaining photoreceptors was restored to normal. At least for the stages of disease studied, this therapeutic vector was highly effective, and warrants further studies for translational applications. In both models, treatment with the hIRPB-hRPGR therapeutic vector prevented (XLPRA1) or reversed (XLPRA2) rod and R/G cone opsin mislocalization, a feature of the disease in human, mouse and dog, and a putative early marker of photoreceptor cell death.

A characteristic feature of photoreceptor degenerations is progressive changes in the OPL, bipolar cells and inner retinal layers. These were widespread in untreated areas, but reversed to normal in treated areas, particularly when the AAV2/5-hIRPB-hRPGR vector was used. Prevention of remodeling occurred when treating XLPRA1 retinas prior to disease onset, while in XLPRA2, early OPL synaptic changes, bipolar cell abnormalities, and inner retinal abnormalities were abrogated with treatment, and normal structure ensued. Thus treatment of the primary photoreceptor defect has beneficial downstream effects as OPL and inner retinal abnormalities are prevented or reversed. This may account for the improved post-receptoral responses recorded from 3 of the 4 treated dogs. Future studies should extend the post-treatment follow-up period to older ages when degeneration of untreated regions would allow testing of treatment consequences at the visual brain such as with the use of pupillometry and visual evoked potentials, and ultimately with visual behavior. Subretinal treatment in XLPRA canine models of RPGRORF15-XLRP with AAV2/5 vectors and the full length human RPGRORF15 cDNA was effective in preserving photoreceptor structure and function.

EXAMPLE 8

Corrective Gene Therapy for RPGR-XLRP Rescues Canine Model at Mid-Stage Disease

The inventors next investigated whether gene therapy delivered at a more advanced stage of disease can still provide a positive outcome. An AAV2/5 vector construct (titer: 1.51×10 vg/ml) carrying full-length human RPGRORF15 cDNA under the control of a hIRBP promoter was injected subretinally in three 12-wk-old XLPRA2 dogs. At that age, there is on-going cell death and the ONL thickness is reduced by ~40%. In addition, one XLPRA2 dog was injected shortly after the onset of disease (5.1 wks of age) as an early disease stage control. Contra-lateral eyes were either injected with BSS, or received a similar dose of viral construct intravitreally. Photoreceptor structure and function was assessed by means of non-invasive retinal imaging (cSLO/SD-OCT) and ERG at 39 and 42 weeks of age, respectively.

In vivo retinal imaging showed preserved ONE thickness in the treated retinal areas. Rod and cone ERG function was greater in treated than in control eyes. Both ONL thickness and ERG responses were better preserved in the animal treated at 5.1 weeks than in the 3 dogs injected at 12 weeks of age.

These results show that a sustained and beneficial effect on photoreceptor structure and retinal function can be achieved even when delivering RPGR acne augmentation at a mid-stage of XLRP disease. This has important translational application given that patients are likely to have more advanced disease at the time of treatment.

Without further description, it is believed that one of ordinary skill in the art can, using the preceding description and illustrative examples, make and utilize the compositions of the present invention and practice the claimed methods. While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art.

The disclosures of Beltran W A, et al, (2012 January) Proc Natl Acad Sci USA, 109(6):2132-7 and U.S. Provisional Patent Application No. 61/670,355, as well as all patents, patent applications and other references, including the Sequence Listing cited in this specification are hereby incorporated by reference in their entirety.

REFERENCES

1. Wright A F, Chakarova C F, Abd El-Aziz M M, & Bhattacharya S S (2010) Photoreceptor degeneration: genetic and mechanistic dissection of a complex trait. Nat Rev Genet 11:273-284.

2. Bramall A N, Wright A F, Jacobson S G, & McInnes R R (2010) The genomic, biochemical, and cellular responses of the retina in inherited photoreceptor degenerations and prospects for the treatment of these disorders. Annu Rev Neurosci 33:441-472.

3. Acland G M, et al. (2001) Gene therapy restores vision in a canine model of childhood blindness. Nature Genetics 28:92-95.

4. Cideciyan A V (2010) Leber congenital amaurosis due to RPE65 mutations and its treatment with gene therapy. Prog Retin Eye Res 29:398-427.

5. Bird A C (1975) X-linked retinitis pigmentosa, Br J Ophthalmol 59:177-199.

6. Bhattacharya S S, et al. (1984) Close genetic linkage between X-linked retinitis pigmentosa and a restriction fragment length polymorphism identified by recombinant DNA probe L1.28. Nature 309:253-255.

7. Meindl A, et al. (1996) A gene (RPGR) with homology to the RCC1 guanine nucleotide exchange factor is mutated in X-linked retinitis pigmentosa (RP3). Nat Genet 13:35-42.

8. Schwahn U, et al. (1998) Positional cloning of the gene for X-linked retinitis pigmentosa 2. Nat Genet 19:327-332.

9. Bader I, et al. (2003) X-linked retinitis pigmentosa: RPGR mutations in most families with definite X linkage and clustering of mutations in a short sequence stretch of exon ORF15. Invest. Ophthahnol. Vis. Sci. 44:1458-1463.

10. Sharon D, et al, (2003) RP2 and RPGR Mutations and Clinical Correlations in Patients with X-Linked Retinitis Pigmentosa. Am Hum Genet 73:1131-1146.

11. Pelletier V, et al. (2007) Comprehensive survey of mutations in RP2 and RPGR in patients affected with distinct retinal dystrophies: genotype-phenotype correlations and impact on genetic counseling. Hum Mutat 28:81-91.

12. Vervoort R, et al, (2000) Mutational hot spot within a new RPGR exon in X-linked retinitis pigmentosa. Nat Genet 25:462-466.

13. Breuer D K, et al. (2002) A comprehensive mutation analysis of RP2 and RPGR in a North American cohort of families with X-linked retinitis pigmentosa. Am J Hum Genet 70:1545-1554.

14. Jacobson S G, et al. (1997) Disease expression in X-linked retinitis pigmentosa caused by a putative null mutation in the RPGR gene. Invest Ophthalmol Vis Sci 38:1983-1997.

15. Sandberg M A, Rosner B, Weigel-DiFranco C, Dryja T P, & Berson E L (2007) Disease course of patients with X-linked retinitis pigmentosa due to RPGR gene mutations. Invest Ophdialmol Vis Sci 48:1298-1304.

16. Aleman T S, et al. (2007) Inner retinal abnormalities in X-linked retinitis pigmentosa with RPGR mutations. Invest Ophthalmol Vis Sci 48:4759-4765.

17. Hong D H, et al. (2000) A retinitis pigmentosa GTPase regulator (RPGR)-deficient mouse model for X-linked retinitis pigmentosa (RP3) Proe Natl Acad Sci USA 97:3649-3654.

18. Chang B, et al. (2002) Retinal degeneration mutants in the mouse. Vision Res 42:517-525.

19. Hong D H, Pawlyk B S, Adamian M, & Li T (2004) Dominant, gain-of-function mutant produced by truncation of RPGR. Invest Ophthalmol Vis Sci 45:36-41.

20. Zhang Q, et al. (2002) Different RPGR exon ORF15 mutations in Canids provide insights into photoreceptor cell degeneration. Human Molecular Genetics 11:993-1003.

21. Zeiss C J, Acland G M, & Aguirre G D (1999) Retinal pathology of canine X-linked progressive retinal atrophy, the locus homologue of RP3. Investigative Ophthalmology & Visual Science 40:3292-3304.

22. Beltran W A, Hammond P, Acland G M, & Aguirre G D (2006) A frameshift mutation in RPGR exon ORE15 causes photoreceptor degeneration and inner retina remodeling in a model of X-linked retinitis pigmentosa, Invest Oplithalmol Vis Sci 47:1669-1681.

23. Wright A F, et al. (2004) Lifespan and mitochondrial control of neurodegeneration. Nat Genet 36:1153-1158.

24. Jacobson S G, et al. (2011) Human retinal disease from AIPL1 gene mutations: foveal cone loss with minimal macular photoreceptors and rod function remaining. Invest Ophthahnol Vis Sci 52:70-79.

25. Ayyagari R, et al. (2002) X-linked recessive atrophic macular degeneration from RPGR mutation. Genomics 80:166-171.

26. Ebenezer N D, et al. (2005) Identification of novel RPGR ORF15 mutations in Xlinked proaressive cone-rod dystrophy (XLCORD) families. Invest Ophthalmol Vis Sci 46:1891-1898.

27. Shu X, et al. (2007) RPGR mutation analysis and disease: an update. Hum Mutat 28:322-328.

28. Walia S, et al. (2008) Discordant phenotypes in fraternal twins having an identical mutation in exon ORF15 of the RPGR gene. Arch Ophthalmol 126:379-384.

29. Ruddle J B, et al. (2009) RPGR ORF15 genotype and clinical variability of retinal degeneration in an Australian population. Br J Ophthalmol 93:1151-1154.

30. Fahim A T, et al. (2011) Allelic heterogeneity and genetic modifier loci contribute to clinical variation in males with X-linked retinitis pigmentosa due to RPGR mutations, PLoS One 6:e23021.

31. Mowat F M, et al. (2008) Topographical characterization of cone photoreceptors and the area centralis of the canine retina. Mol Vis 14:2518-2527.

32. Acland G M, et al. (2005) Long-term restoration of rod and cone vision by single dose rAAV-mediated gene transfer to the retina in a canine model of childhood blindness. Mol Ther 12:1072-1082.

33. Khanna H, et al, (2005) RPGR-ORF15, which is mutated in retinitis pigmentosa, associates with SMC1, SMC3, and microtubule transport proteins. J Biol. Chem 280:33580-33587.

34. Adamian M, Pawlyk B S, Hong D H, & Berson E L (2006) Rod and cone opsin mislocalization in an autopsy eye from a carrier of X-linked retinitis pigmentosa with a Gly436Asp mutation in the RPGR gene, Am J Ophthahnol 142:515-518.

35. Beltran W A, Acland G M, & Aguirre G D (2009) Age-dependent disease expression determines remodeling of the retinal mosaic in carriers of RPGR exon ORF15 mutations. Invest Ophthalinol Vis Sci 50:3985-3995.

36. Aguirre G D, et al. (2002) Retinal histopathology of an XLRP carrier with a mutation in the RPGR exon ORE15. Exp Eye Res 75:431-443.

37. Li Z Y, Kljavin I J, & Milam A H (1995) Rod photoreceptor neurite sprouting in retinitis pigmentosa. J Neurosci 15:5429-5438.

38. Geiger K, et al. (1994) Transgenic mice expressing IFN-gamma in the retina develop inflammation of the eye and photoreceptor loss. Invest Ophthalmol Vis Sci 35:2667-2681.

39. Jacobson S G & Cideciyan A V (2010) Treatment possibilities for retinitis pigmentosa. N Engl J Med 363:1669-1671, 40. Wright A F & Shu X (2007) Focus on Molecules: RPGR. Exp Eye Res 85:1-2.

41. Simons D L. Hoye S L, Hauswirth W W, & Wu S M (2011) Gene therapy prevents photoreceptor death and preserves retinal function in a Bardet-Biedl syndrome mouse model. Proe Natl Acad Sci USA 108:6276-6281.

42. Guyon R, Pearce-Kelling S E, Zeiss C J, Acland G M, & Aguirre C D (2007) Analysis of six candidate genes as potential modifiers of disease expression in canine XLPRA1, a model for human X-linked retinitis pigmentosa 3. Mol Vis 13:1094-1105.

43. Demirel F Y, et al. (2002) X-linked cone-rod dystrophy (locus COD1): identification of mutations in RPGR exon ORF15. Am J Hum Genet 70:1049-1053.

44. Yang Z, et al. (2002) Mutations in the RPGR gene cause X-linked cone dystrophy. Hum Mol Genet 11:605-611.

45. Demirci F Y, et al. (2005) Histopathologic study of X-linked cone-rod dystrophy (CORDX1) caused by a mutation in the RPGR exon ORE15. Am J Ophthalmol 139:386-388.

46. Alexander J J, et (2007) Restoration of cone vision in a mouse model of achromatopsia. Nat Med 13:685-687.

47. Komaromy A M, et al. (2010) Gene therapy rescues cone function in congenital achromatopsia. Hum Mol Genet 19:2581-2593.

48. Michalakis S, et al. (2010) Restoration of cone vision in the CNGA3−/− mouse model of congenital complete lack of cone photoreceptor function. Mol Ther 18:2057-2063.

49. Caryalho L S, et al. (2011) Long-term and age-dependent restoration of visual function in a mouse model of CNGB3-associated achromatopsia following gene therapy. Hum Mol Genet 20:3161-3175.

50. Jacobson S G, et al. (2011) Gene Therapy for Leber Congenital Amaurosis Caused by RPE65 Mutations: Safety and Efficacy in 15 Children and Adults Followed Up to 3 Years. Arch Ophthalmol E published ahead of print.

51. Petrs-Silva H, et al, (2011) Novel properties of tyrosine-mutant AAV2 vectors in the mouse retina. Mol Ther 19:293-301.

52. He S, et al. (2008) Retinitis Pigmentosa GTPase Regulator (RPGR) protein isoforms in mammalian retina: insights into X-linked Retinitis Pigmentosa and associated ciliopathies. Vision Res 48:366-376.

53. Murga-Zamalloa C A, Desai N J, Hildebrandt F, & Khanna H (2010) Interaction of ciliary disease protein retinitis pigmentosa GTPase regulator with nephronophthisis-associated proteins in mammalian retinas. Mol Vis 16:1373-1381.

54. Shu X, et al. (2005) RPGR ORF15 isoform co-localizes with RPGRIP1 at centrioles and basal bodies and interacts with nucleophosmin. Hum Mol Genet 14:1183-1197.

55. Murga-Zamalloa C A, Aktkins S J, Peranen J, Swaroop A, & Khanna H (2010) Interaction of retinitis pigmentosa GTPase regulator (RPGR) with RAB8A GTPase: implications for cilia dysfunction and photoreceptor degeneration. Hum Mol Genet 19:3591-3598.

56. Ghosh A K, et al, (2010) Human retinopathy-associated ciliary protein Retinitis Pigmentosa GTPase Regulator mediates cilia-dependent vertebrate development. Hum Mol Genet 19:90-98.

57. Porrello K, Bhat S P, & Bok D (1991) Detection of interphotoreceptor retinoid binding protein (IRBP) mRNA in human and cone-dominant squirrel retinas by in situ hybridization. J Histochem Cytochem 39:171-176.

58. Alfinito P D & Townes-Anderson E (2002) Ac,tivation of mislocalized opsin kills rod cells: a novel mechanism for rod cell death in retinal disease. Proc Nat'l Acad Sci USA 99:5655-5660.

59. Zhang T, Zhang N, Baehr W, & Fu Y (2011) Cone opsin determines the time course of cone photoreceptor degeneration in Leber congenital amaurosis. Proc Natl Acad Sci. USA 108:8879-8884.

60. Jacobson S G, et al. (2009) Disease boundaries in the retina of patients with Usher syndrome caused by MYO7A gene mutations. Invest Ophthalmol Vis Sci 50:1886-1894.

61. Jacobson S G, et al. (2008) Photoreceptor layer topography in children with leber congenital amaurosis caused by RPE65 mutations. Invest Ophthalmol Vis Sci 49:4573-4577.

62. Beltran W A, et al. (2010) rAAV2/5 gene-targeting to rods:dose-dependent efficiency and complications associated with different promoters. Gene Ther 17:1162-1174.

63. Zhang Q, et al. (2002) Different RPGR exon ORF15 mutations in Canids provide insights into photoreceptor cell degeneration. *Human Molecular Genetics* 11:993-1003.

64. Hong D H, Pawlyk B S, .Adamian M, Sandberg M A, & Li T (2005) A single, abbreviated RPGR-ORF15 variant reconstitutes RPGR function in vivo. *Invest Ophthalmol Vis Sci* 46:435-441.

65. Beltran W A, et al. (2010) rAAV2/5 gene-targeting to rods:dose-dependent efficiency and complications associated with different promoters. *Gene Ther* 17:1162-1174.

What is claimed is:

1. A recombinant adeno-associated virus (AAV) carrying a nucleic acid sequence encoding a human retinitis pigmentosa GTPase regulator (RPGR) gene product, under the control of regulatory sequences which express the gene product in the photoreceptor cells of a subject in need thereof, wherein the nucleic acid sequence comprises the sequence of SEQ ID NO: 1.

2. The AAV according to claim 1, wherein the regulatory sequences comprise the interphotoreceptor retinoid-binding protein proximal promoter or G-protein-coupled receptor protein kinase 1 promoter.

3. The AAV according to claim 1, wherein the AAV is an AAV2/5 pseudotyped AAV.

4. A recombinant adeno-associated virus (AAV) carrying a nucleic acid sequence encoding a human retinitis pigmentosa GTPase regulator (RPGR) gene product, under the control of regulatory sequences which express the gene product in the photoreceptor cells of a subject in need thereof, wherein the nucleic acid sequence encodes the sequence of SEQ ID NO: 5.

5. The AAV according to claim 1, wherein the AAV is an AAV2.

6. A recombinant adeno-associated virus (AAV) carrying a nucleic acid sequence encoding a human retinitis pigmentosa GTPase regulator (RPGR) gene product, under the control of regulatory sequences which express the gene product in the photoreceptor cells of a subject in need thereof, wherein the nucleic acid sequence comprises a codon optimized variant of the sequence of SEQ ID NO:1, which encodes the sequence of SEQ ID NO: 5.

7. The AAV according to claim 6, wherein the regulatory sequences comprise the interphotoreceptor retinoid-binding protein proximal promoter or G-protein-coupled receptor protein kinase 1 promoter.

8. The AAV according to claim 6, wherein the AAV is an AAV2/5 pseudotyped AAV.

9. The AAV according to claim 6, wherein the AAV is an AAV2.

10. The AAV according to claim 4, wherein the regulatory sequences comprise the interphotoreceptor retinoid-binding protein proximal promoter or G-protein-coupled receptor protein kinase 1 promoter.

11. The AAV according to claim 4, wherein the AAV is an AAV2/5 pseudotyped AAV.

12. The AAV according to claim 4, wherein the AAV is an AAV2.

* * * * *

SEQUENCE LISTING

```
<160> NUMBER OF SEQ ID NOS: 7

<210> SEQ ID NO 1
<211> LENGTH: 3417
<212> TYPE: DNA
<213> ORGANISM: Homo sapiens

<400> SEQUENCE: 1
atgagggagc cggaagagct gatgcccgat tcgggtgctg tgtttacatt tgggaaaagt      60
aaatttgctg aaaataatcc cggtaaattc tggtttaaaa atgatgtccc tgtacatctt     120
tcatgtggag atgaacattc tgctgttgtt accggaaata ataaacttta catgtttggc     180
agtaacaact ggggtcagtt aggattagga tcaaagtcag ccatcagcaa gccaacatgt     240
gtcaaagctc taaaacctga aaaagtgaaa ttagctgcct gtggaaggaa ccacaccctg     300
gtgtcaacag aaggaggcaa tgtatatgca actggtggaa ataatgaagg acagttgggg     360
cttggtgaca ccgaagaaag aaacactttt catgtaatta gcttttttac atccgagcat     420
aagattaagc agctgtctgc tggatctaat acttcagctg ccctaactga ggatggaaga     480
ctttttatgt ggggtgacaa ttccgaaggg caaattggtt taaaaaatgt aagtaatgtc     540
tgtgtccctc agcaagtgac cattgggaaa cctgtctcct ggatctcttg tggatattac     600
cattcagctt ttgtaacaac agatggtgag ctatatgtgt tggagaacc tgagaatggg     660 aagttaggtc ttcccaatca gctcctgggc aatcacagaa caccccagct ggtgtctgaa     720
attccggaga aggtgatcca agtagcctgt ggtgagagc atactgtggt tctcacggag     780
aatgctgtgt atacctttgg gctgggacaa tttggtcagc tgggtcttgg cactttctt     840 tttgaaactt cagaacccaa agtcattgag aatattaggg atcaaacaat aagttatatt     900
tcttgtggag aaaatcacac agctttgata acagatatcg gccttatgta tactttgga     960
```

```
gatggtcgcc acggaaaatt aggacttgga ctggagaatt ttaccaatca cttcattcct   1020
actttgtgct ctaattttt gaggtttata gttaaattgg ttgcttgtgg tggatgtcac    1080
atggtagttt ttgctgctcc tcatcgtggt gtggcaaaag aaattgaatt cgatgaaata   1140
aatgacactt gcttatctgt ggcgactttt ctgccgtata gcagtttaac ctcaggaaat   1200
gtactgcaga ggactctatc agcacgtatg cggcgaagag agagggagag gtctccagat   1260 tcttttcaa tgaggagaac actacctcca atagaaggga ctcttggcct ttctgcttgt    1320
tttctcccca attcagtctt tccacgatgt tctgagagaa acctccaaga gagtgtctta   1380
tctgaacagg acctcatgca gccagaggaa ccagattatt tgctagatga aatgaccaaa   1440
gaagcagaga tagataattc ttcaactgta gaaagccttg agaaactac tgatatctta    1500 aacatgacac acatcatgag cctgaattcc aatgaaaagt cattaaaatt atcaccagtt   1560
cagaaacaaa agaaacaaca acaattggg gaactgacgc aggatacagc tcttactgaa    1620
aacgatgata gtgatgaata tgaagaaatg tcagaaatga agaagggaa agcatgtaaa    1680 caacatgtgt cacaagggat tttcatgacg cagccagcta cgactatcga agcattttca   1740
gatgaggaag tagagatccc agaggagaag aaggagcag aggattcaaa aggaaatgga    1800
atagaggagc aagaggtaga agcaaatgag gaaaatgtga aggtgcatgg aggaagaaag   1860
gagaaaacag agatcctatc agatgaccttt acagacaaag cagaggtgag tgaaggcaag   1920
gcaaaatcag tgggagaagc agaggatggg cctgaaggta gaggggatgg aacctgtgag   1980
gaaggtagtt caggagcaga acactggcaa gatgaggaga gggagaaggg ggagaaagac   2040
aagggtagag gagaaatgga gaggccagga gaggggggaga aggaactagc agagaaggaa   2100
gaatggaaga gagggatgg ggaagagcag gagcaaaagg agagggagca gggccatcag    2160
aaggaaagaa accaagagat ggaggaggga ggggaggagg agcatggaga aggagaagaa   2220
gaggagggag acagagaaga ggaagaagag aaggaggag aagggaaaga ggaaggagaa    2280
ggggaagaag tggaggggaga acgtgaaaag gaggaaggag agaggaaaaa ggaggaagaa   2340
gcggggaagg aggagaaagg agaggaagaa ggagaccaag gagagggggga agaggaggaa   2400 acagagggga gaggggagga aaagaggag ggaggggaag tagagggagg ggaagtagag     2460
gaggggaaag gagagagggga agaggaagag gaggagggtg aggggggaaga ggaggaaggg   2520 gaggggggaag aggaggaagg agaagggaaa ggggaggaag aagggggaaga aggagaaggg   2580 gaggaagaag gggaggaagg agaaggggag ggggaagagg aggaaggaga aggggaggga   2640
gaagaggaag gagaagggga ggaagaagga gaggagagg aagaagggga gggagaaggg    2700
gaggaagaag aggaagggga agtggaaggg gaggtggaag gggaggaagg agaggggaa    2760 ggagaggaag aggaaggaga ggaggaagga gaggaagagg aaggagagga ggaaggagag   2820
gaagaggaag gagaggaaga ggaaggagag gaggaaggag aggaaggaga aggggagggg   2880
gaagaggagg aaggagaagg ggaaggggag gatggagaag ggagggggga aggagaggaa   2940
gaggaaggag aggaggaagg agaagaaagg gaaaaggagg gggaaggaga ggaagaggaa   3000
ggagaggagg aaggggaagt ggaagggga gtggaagggg aggaaggaga ggggaaggaa    3060
gaggaagagg aaggagagga ggaaggagaa gaaagggaaa aggagggga aggagaagaa    3120 aacaggagga acagagaaga ggaggaggaa gaagagggga agtatcagga gacaggcgaa   3180
gaagagaatg aaaggcagga tggagaggag tacaaaaaag tgagcaaaat aaaaggatct   3240
gtgaaatatg gcaaacataa aacatatcaa aaaagtcag ttactaacac acagggaaat    3300
gggaaagagc agaggtccaa aatgccagtc cagtcaaaac gacttttaaa aaacgggcca   3360
```

```
tcaggttcca aaaagttctg aataatgta ttaccacatt acttggaatt gaagtaa        3417
```

<210> SEQ ID NO 2
<211> LENGTH: 292
<212> TYPE: DNA
<213> ORGANISM: Homo sapiens

<400> SEQUENCE: 2

```
gggcccaga agcctggtgg ttgtttgtcc ttctcagggg aaaagtgagg cggccccttg      60
gaggaagggg ccgggcagaa tgatctaatc ggattccaag cagctcaggg gattgtcttt   120
ttctagcacc ttcttgccac tcctaagcgt cctccgtgac cccggctggg atttagcctg   180
gtgctgtgtc agccccggtc tcccaggggc ttcccagtgg tccccaggaa ccctcgacag   240
ggcccggtct ctctcgtcca gcaagggcag ggacgggcca caggccaagg gc           292
```

<210> SEQ ID NO 3
<211> LENGTH: 235
<212> TYPE: DNA
<213> ORGANISM: Homo sapiens

<400> SEQUENCE: 3

```
agcacagtgt ctggcatgta gcaggaacta aaataatggc agtgattaat gttatgatat    60
gcagacacaa cacagcaaga taagatgcaa tgtaccttct gggtcaaacc accctggcca   120
ctcctccccg atacccaggg ttgatgtgct tgaattagac aggattaaag cttactgga    180
gctggaagcc ttgccccaac tcaggagttt agccccagac cttctgtcca ccagc        235
```

<210> SEQ ID NO 4
<211> LENGTH: 3456
<212> TYPE: DNA
<213> ORGANISM: Homo sapiens

<400> SEQUENCE: 4

```
atgagggagc cggaagagct gatgcccgat tcgggtgctg tgtttacatt tgggaaaagt    60
aaatttgctg aaaataatcc cggtaaattc tggtttaaaa atgatgtccc tgtacatctt   120
tcatgtggag atgaacattc tgctgttgtt accggaaata taaactttta catgtttggc   180
agtaacaact ggggtcagtt aggattagga tcaaagtcag ccatcagcaa gccaacatgt   240
gtcaaagctc taaaacctga aaagtgaaa ttagctgcct gtggaaggaa ccacaccctg    300
gtgtcaacag aaggaggcaa tgtatatgca actggtggaa ataatgaagg acagttgggg   360
cttggtgaca ccgaagaaag aaacactttt catgtaatta gctttttac atccgagcat    420
aagattaagc agctgtctgc tggatctaat acttcagctg ccctaactga ggatggaaga   480
ctttttatgt ggggtgacaa ttccgaaggg caaattggtt taaaaatgt aagtaatgtc    540
tgtgtccctc agcaagtgac cattgggaaa cctgtctcct ggatctcttg tggatattac   600
cattcagctt tgtaacaac agatggtgag ctatatgtgt ttggagaacc tgagaatggg   660
aagttaggtc ttcccaatca gctcctgggc aatcacagaa caccccagct ggtgtctgaa   720
attccggaga aggtgatcca agtagcctgt ggtggagagc atactgtggt tctcacggag   780
aatgctgtgt atacctttgg gctgggacaa tttggtcagc tgggtcttgg cacttttctt   840
tttgaaactt cagaacccaa agtcattgag aatattaggg atcaaacaat aagttatatt   900
tcttgtggag aaaatcacac agctttgata acagatatcg gccttatgta acttttgga    960
gatggtcgcc acggaaaatt aggacttgga ctggagaatt ttaccaatca cttcattcct  1020
```

```
actttgtgct ctaatttttt gaggtttata gttaaattgg ttgcttgtgg tggatgtcac    1080
atggtagttt ttgctgctcc tcatcgtggt gtggcaaaag aaattgaatt cgatgaaata    1140
aatgatactt gcttatctgt ggcgactttt ctgccgtata gcagtttaac ctcaggaaat    1200
gtactgcaga ggactctatc agcacgtatg cggcgaagag agagggagag gtctccagat    1260 tcttttttcaa tgaggagaac actacctcca atagaaggga ctcttggcct ttctgcttgt    1320
tttctcccca attcagtctt tccacgatgt tctgagagaa acctccaaga gagtgtctta    1380
tctgaacagg acctcatgca gccagaggaa ccagattatt gctagatga aatgaccaaa    1440 gaagcagaga tagataattc ttcaactgta gaaagccttg gagaaactac tgatatctta    1500
aacatgacac acatcatgag cctgaattcc aatgaaaagt cattaaaatt atcaccagtt    1560
cagaaacaaa agaaacaaca acaattggg gaactgacgc aggatacagc tcttactgaa    1620
aacgatgata gtgatgaata tgaagaaatg tcagaaatga agaagggaa agcatgtaaa    1680 caacatgtgt cacaagggat tttcatgacg cagccagcta cgactatcga agcattttca    1740
gatgaggaag tagagatccc agaggagaag gaaggagcag aggattcaaa aggaaatgga    1800
atagaggagc aagaggtaga agcaaatgag gaaaatgtga aggtgcatgg aggaagaaag    1860
gagaaaacag agatcctatc agatgaccct acagacaaag cagaggtgag tgaaggcaag    1920
gcaaaatcag tgggagaagc agaggatggg cctgaaggta gagggatgg aacctgtgag    1980 gaaggtagtt caggagcaga acactggcaa gatgaggaga gggagaaggg ggagaaagac    2040
aagggtagag gagaaatgga gaggccagga gagggagaga aggaactagc agagaaggaa    2100
gaatggaaga gagggatgg ggaagagcag gagcaaaagg agagggagca gggccatcag    2160
aaggaaagaa accaagagat ggaggaggga ggggaggagg agcatggaga aggagaagaa    2220
gaggagggag acagagaaga ggaagaagag aaggagggag aagggaaaga ggaaggagaa    2280
ggggaagaag tggagggaga acgtgaaaag gaggaaggag agaggaaaaa ggaggaaaga    2340
gcggggaagg aggagaaagg agaggaagaa ggagaccaag gagaggggga gaggaggaa    2400 acagagggga gaggggagga aaaagaggag ggaggggaag tagagggagg ggaagtagag    2460 gagggggaaag gagagagggga agaggaagag gaggagggtg aggggggaaga ggaggaaggg    2520 gaggggggaag aggaggaagg ggaggggggaa gaggaggaag gagaagggaa aggggaggaa    2580
gaaggggaag aaggagaagg ggaggaagaa ggggaggaag gagaaggga ggggaagag    2640 gaggaaggag aagggaggg agaagaggaa ggagaagggg aggggagaaga ggaggaagga    2700 gaaggggagg gagaagagga aggagaaggg ggaggggagaag aggaggaagg agaagggaaa    2760
ggggaggagg aaggagagga aggagaaggg gaggggggaag gaggaggaagg agaagggggaa    2820 ggggaggatg gagaagggga ggggggaagag gaggaaggaa aatgggaggg ggaggaggaa    2880
ggagaagggg aggggggaaga ggaaggagaa ggggaagggg aggaaggaga aggggaggg    2940 gaagaggagg aaggagaagg ggaggggggaa ggaggaggaag gggaagaaga aggggaggaa    3000
gaaggagagg gagaggaaga aggggaggga gaagggggagg aagaagagga aggggaagtg    3060 gaagggggagg tggaagggga ggaaggagag ggggaaggag aggaagagga aggagaggag    3120
gaaggagaag aaagggaaaa ggagggggaa ggagaagaaa acaggaggaa cagagaagag    3180
gaggaggaag aagagggggaa gtatcaggag acaggcgaag aagagaatga aaggcaggat    3240
ggagaggagt acaaaaaagt gagcaaaata aaaggatctg tgaaatatgg caaacataaa    3300
acatatcaaa aaaagtcagt tactaacaca cagggaaatg ggaaagagca gaggtccaaa    3360
atgccagtcc agtcaaaacg acttttaaaa aacgggccat caggttccaa aaagttctgg    3420
```

```
aataatgtat taccacatta cttggaattg aagtaa                              3456
```

<210> SEQ ID NO 5
<211> LENGTH: 1138
<212> TYPE: PRT
<213> ORGANISM: Homo sapiens

<400> SEQUENCE: 5

```
Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
        35                  40                  45

Val Val Thr Gly Asn Asn Lys Leu Tyr Met Phe Gly Ser Asn Asn Trp
    50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
        275                 280                 285

Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
        355                 360                 365
```

```
Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
                435                 440                 445

Arg Cys Ser Glu Arg Asn Leu Gln Glu Ser Val Leu Ser Glu Gln Asp
    450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Lys Gln Gln Thr
    515                 520                 525

Ile Gly Glu Leu Thr Gln Asp Thr Ala Leu Thr Glu Asn Asp Asp Ser
    530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
                580                 585                 590

Ala Glu Asp Ser Lys Gly Asn Gly Ile Glu Glu Gln Glu Val Glu Ala
                595                 600                 605

Asn Glu Glu Asn Val Lys Val His Gly Gly Arg Lys Glu Lys Thr Glu
    610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu
                660                 665                 670

Glu Arg Glu Lys Gly Glu Lys Asp Lys Gly Arg Gly Glu Met Glu Arg
    675                 680                 685

Pro Gly Glu Gly Glu Lys Glu Leu Ala Glu Lys Glu Glu Trp Lys Lys
    690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Glu Glu Glu His Gly
                725                 730                 735

Glu Gly Glu Glu Glu Gly Gly Asp Arg Glu Glu Glu Glu Lys Glu
            740                 745                 750

Gly Glu Gly Lys Glu Glu Gly Glu Gly Glu Glu Val Glu Gly Glu Arg
                755                 760                 765

Glu Lys Glu Glu Gly Glu Arg Lys Lys Glu Glu Arg Ala Gly Lys Glu
    770                 775                 780
```

Glu Lys Gly Glu Glu Gly Asp Gln Gly Glu Glu Glu Glu
785                 790                 795                 800

Thr Glu Gly Arg Gly Glu Lys Glu Gly Gly Glu Val Glu Gly
            805                 810                 815

Gly Glu Val Glu Glu Gly Lys Gly Arg Glu Glu Glu Glu Glu
            820                 825                 830

Gly Glu Gly Glu Glu Glu Glu Gly Glu Glu Glu Glu Gly Glu
            835                 840                 845

Gly Lys Gly Glu Glu Gly Glu Glu Glu Glu Glu Glu Glu Gly
    850                 855                 860

Glu Glu Gly Glu Gly Glu Glu Glu Glu Gly Glu Gly Glu Gly
865                 870                 875                 880

Glu Glu Glu Gly Glu Gly Glu Glu Glu Gly Glu Glu Glu Gly
                885                 890                 895

Glu Gly Glu Gly Glu Glu Glu Glu Gly Glu Val Glu Gly Glu Val
                900                 905                 910

Glu Gly Glu Glu Glu Gly Glu Glu Glu Gly Glu Glu Glu Glu
                915                 920                 925

Glu Gly Glu Glu Glu Gly Glu Glu Glu Gly Glu Gly Glu Glu
    930                 935                 940

Glu Glu Glu Glu Gly Glu Glu Glu Gly Glu Gly Glu Glu Gly
945                 950                 955                 960

Glu Glu Glu Glu Gly Glu Glu Gly Glu Asp Gly Glu Glu Gly
                965                 970                 975

Glu Gly Glu Glu Glu Gly Glu Glu Glu Gly Glu Glu Arg Glu Lys
                980                 985                 990

Glu Gly Glu Gly Glu Glu Glu Glu Gly Glu Glu Glu Gly Glu Val Glu
        995                 1000                1005

Gly Glu Val Glu Gly Glu Glu Gly Glu Gly Glu Gly Glu Glu Glu
    1010                1015                1020

Glu Gly Glu Glu Glu Gly Glu Glu Arg Glu Lys Glu Gly Glu Gly
    1025                1030                1035

Glu Glu Asn Arg Arg Asn Arg Glu Glu Glu Glu Glu Glu Glu Gly
    1040                1045                1050

Lys Tyr Gln Glu Thr Gly Glu Glu Glu Asn Glu Arg Gln Asp Gly
    1055                1060                1065

Glu Glu Tyr Lys Lys Val Ser Lys Ile Lys Gly Ser Val Lys Tyr
    1070                1075                1080

Gly Lys His Lys Thr Tyr Gln Lys Lys Ser Val Thr Asn Thr Gln
    1085                1090                1095

Gly Asn Gly Lys Glu Gln Arg Ser Lys Met Pro Val Gln Ser Lys
    1100                1105                1110

Arg Leu Leu Lys Asn Gly Pro Ser Gly Ser Lys Phe Trp Asn
    1115                1120                1125

Asn Val Leu Pro His Tyr Leu Glu Leu Lys
    1130                1135

<210> SEQ ID NO 6
<211> LENGTH: 1152
<212> TYPE: PRT
<213> ORGANISM: HOMO SAPIENS

<400> SEQUENCE: 6

Met Arg Glu Pro Glu Glu Leu Met Pro Asp Ser Gly Ala Val Phe Thr
1               5                   10                  15

```
Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
    50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
    195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
    275                 280                 285

Ile Glu Asn Ile Arg Asp Gln Thr Ile Ser Tyr Ile Ser Cys Gly Glu
            290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
            420                 425                 430
```

```
Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
            515                 520                 525

Ile Gly Glu Leu Thr Gln Asp Thr Ala Leu Thr Glu Asn Asp Asp Ser
530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
            595                 600                 605

Asn Glu Glu Asn Val Lys Val His Gly Gly Arg Lys Glu Lys Thr Glu
            610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu
            660                 665                 670

Glu Arg Glu Lys Gly Glu Lys Asp Lys Gly Arg Gly Glu Met Glu Arg
            675                 680                 685

Pro Gly Glu Gly Glu Lys Glu Leu Ala Glu Lys Glu Glu Trp Lys Lys
            690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Glu Glu Glu His Gly
                725                 730                 735

Glu Gly Glu Glu Glu Gly Asp Arg Glu Glu Glu Glu Lys Glu
            740                 745                 750

Gly Glu Gly Lys Glu Glu Gly Gly Glu Glu Val Glu Gly Glu Arg
            755                 760                 765

Glu Lys Glu Glu Gly Glu Arg Lys Lys Glu Glu Arg Ala Gly Lys Glu
            770                 775                 780

Glu Lys Gly Glu Glu Glu Gly Asp Gln Gly Glu Gly Glu Glu Glu
785                 790                 795                 800

Thr Glu Gly Arg Gly Glu Glu Lys Glu Glu Gly Gly Glu Val Glu Gly
                805                 810                 815

Gly Glu Val Glu Glu Gly Lys Gly Glu Arg Glu Glu Glu Glu Glu
            820                 825                 830

Gly Glu Gly Glu Glu Gly Glu Gly Glu Glu Glu Glu Gly Glu
            835                 840                 845

Gly Glu Glu Glu Glu Gly Glu Gly Lys Gly Glu Glu Glu Gly Glu Glu
```

850                 855                 860

Gly Glu Gly Glu Glu Glu Glu Gly Glu Glu Glu Glu Glu Glu Glu Glu
865                 870                 875                 880

Glu Glu Gly Glu Gly Glu Glu Glu Glu Gly Glu Gly Glu Gly Glu Glu
                885                 890                 895

Glu Glu Glu Gly Glu Gly Glu Gly Glu Glu Glu Glu Gly Glu Glu Gly
            900                 905                 910

Glu Glu Glu Glu Gly Glu Gly Lys Gly Glu Glu Gly Glu Glu Glu Gly
        915                 920                 925

Glu Gly Glu Gly Glu Glu Glu Gly Glu Gly Glu Gly Glu Asp Gly Glu
    930                 935                 940

Gly Glu Gly Glu Glu Glu Gly Glu Gly Trp Glu Gly Glu Glu Glu Glu
945                 950                 955                 960

Glu Gly Glu Gly Glu Gly Glu Glu Gly Glu Gly Glu Gly Glu Glu Gly
                965                 970                 975

Glu Gly Glu Gly Glu Glu Glu Gly Glu Gly Glu Gly Glu Glu Glu Glu
            980                 985                 990

Glu Glu Gly Glu Glu Glu Gly Glu Glu Glu Gly Glu Gly Glu Glu Glu
        995                 1000                1005

Gly Glu Gly Glu Gly Glu Glu Glu Glu Gly Glu Val Glu Gly Glu Val
    1010                1015                1020

Glu Gly Glu Glu Gly Glu Gly Glu Glu Glu Gly Glu Glu Glu Gly Glu
    1025                1030                1035

Glu Gly Glu Glu Arg Glu Lys Glu Gly Glu Gly Glu Glu Asn Arg Arg
    1040                1045                1050

Asn Arg Glu Glu Glu Glu Glu Glu Gly Lys Tyr Gln Glu Thr Gly Glu
    1055                1060                1065

Glu Asn Glu Arg Gln Asp Gly Glu Glu Tyr Lys Lys Val Ser Lys Ile
        1070                1075                1080

Lys Gly Ser Val Lys Tyr Gly Lys His Lys Thr Tyr Gln Lys Lys Ser
            1085                1090                1095

Val Thr Asn Thr Gln Gly Asn Gly Lys Glu Gln Arg Ser Lys Met Pro
                1100                1105                1110

Val Gln Ser Lys Arg Leu Leu Lys Asn Gly Pro Ser Gly Ser Lys Phe
                    1115                1120                1125

Trp Asn Asn Ile Leu Pro His Tyr Leu Glu Leu Lys
        1130                1135                1140

<210> SEQ ID NO 7
<211> LENGTH: 179
<212> TYPE: PRT
<213> ORGANISM: homo sapiens

<400> SEQUENCE: 7

Glu Glu Gly Glu Gly Lys Gly Glu Glu Gly Glu Glu Gly Glu Gly
1               5                   10                  15

Glu Glu Glu Gly Glu Gly Glu Gly Glu Gly Glu Glu Glu Glu Gly
            20                  25                  30

Glu Gly Glu Gly Glu Glu Glu Gly Glu Gly Glu Glu Glu Gly Glu Gly
        35                  40                  45

Glu Glu Glu Gly Glu Gly Glu Glu Glu Glu Gly Glu Gly Glu Glu
    50                  55                  60

-continued

```
Gly Glu Glu Gly Glu Gly Glu Gly Glu Glu Glu Gly Glu Glu Gly
 65                  70                  75                  80

Glu Asp Glu Gly Glu Glu Glu Glu Glu Glu Gly Glu Glu Glu Glu
                 85                  90                  95

Gly Glu Glu Gly Glu Glu Glu Gly Gly Glu Glu Glu Gly Glu Gly
            100                 105                 110

Glu Gly Glu Asp Glu Gly Glu Gly Glu Glu Glu Glu Glu Gly Glu
            115                 120                 125

Glu Glu Gly Glu Glu Glu Glu Glu Gly Glu Glu Glu Glu Glu Glu
        130                 135                 140

Gly Glu Val Glu Gly Glu Val Glu Gly Glu Glu Gly Glu Gly Glu Gly
145                 150                 155                 160

Glu Glu Glu Glu Gly Glu Glu Glu Gly Glu Glu Arg Glu Lys Glu Gly
            165                 170                 175

Glu Gly Glu
```